(12) United States Patent
Wei et al.

(10) Patent No.: US 7,060,301 B2
(45) Date of Patent: Jun. 13, 2006

(54) IN SITU MONO-OR DIESTER DICARBOXYLATE COMPOSITIONS

(75) Inventors: Guang-Jong Jason Wei, Mendota Heights, MN (US); Larry A. Grab, Woodbury, MN (US); Robert Dale Hei, Baldwin, WI (US); Teresa C. Podtburg, Waconia, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 09/905,189

(22) Filed: Jul. 13, 2001

(65) Prior Publication Data

US 2003/0021853 A1 Jan. 30, 2003

(51) Int. Cl.
*A01N 37/04* (2006.01)
*A01N 37/16* (2006.01)
*A01N 59/00* (2006.01)
*C11D 3/39* (2006.01)

(52) U.S. Cl. ............ 424/616; 424/601; 424/602; 424/603; 424/604; 424/605; 424/606; 514/532; 514/533; 514/546; 514/547; 514/557; 514/558; 514/560; 514/574; 422/29; 510/375; 426/392; 426/397; 426/399

(58) Field of Classification Search ............ 424/616, 424/601–606; 514/557, 558, 560, 574, 547, 514/532, 533, 546; 422/29; 510/375; 426/392, 426/397, 399
See application file for complete search history.

(56) References Cited

U.S. PATENT DOCUMENTS

| | | |
|---|---|---|
| 2,512,640 A | 6/1950 | Greenspan et al. |
| 3,122,417 A | 2/1964 | Blaser et al. |
| 3,248,281 A | 4/1966 | Goodenough |
| 3,350,265 A | 10/1967 | Rubinstein et al. |
| 3,514,278 A | 5/1970 | Brink |
| 3,895,116 A | 7/1975 | Herting et al. |
| 3,996,386 A | 12/1976 | Malkki et al. |
| 4,041,149 A | 8/1977 | Gaffar et al. |
| 4,051,058 A | 9/1977 | Böwing et al. |
| 4,051,059 A | 9/1977 | Böwing et al. |
| 4,129,517 A | 12/1978 | Eggensperger et al. |
| 4,191,660 A | 3/1980 | Schreiber et al. |
| 4,244,884 A | 1/1981 | Hutchins et al. |
| 4,370,199 A | 1/1983 | Orndorff |
| 4,404,040 A | 9/1983 | Wang |
| 4,477,438 A | 10/1984 | Willcockson et al. |
| 4,478,683 A | 10/1984 | Orndorff |
| 4,501,681 A | 2/1985 | Groult et al. |
| 4,529,534 A | 7/1985 | Richardson |
| 4,557,898 A | 12/1985 | Greene et al. |
| 4,592,488 A | 6/1986 | Simon et al. |
| 4,613,452 A | 9/1986 | Sanderson |
| 4,655,781 A | 4/1987 | Hsieh et al. |
| 4,715,980 A | 12/1987 | Lopes et al. |
| 4,738,840 A | 4/1988 | Simon et al. |
| 4,802,994 A | 2/1989 | Mouché et al. |
| 4,865,752 A | 9/1989 | Jacobs |
| 4,900,721 A | 2/1990 | Bansemir et al. |
| 4,906,617 A | 3/1990 | Jacquet et al. |
| 4,908,306 A | 3/1990 | Lorincz |
| 4,917,815 A | 4/1990 | Beilfuss et al. |
| 4,923,677 A | 5/1990 | Simon et al. |
| 4,937,066 A | 6/1990 | Vlock |
| 4,943,414 A | 7/1990 | Jacobs et al. |
| 4,945,110 A | 7/1990 | Brokken et al. |
| 4,996,062 A | 2/1991 | Lehtonen et al. |
| 4,997,571 A | 3/1991 | Roensch et al. |
| 4,997,625 A | 3/1991 | Simon et al. |
| 5,004,760 A | 4/1991 | Patton et al. |
| 5,010,109 A | 4/1991 | Inoi |
| 5,015,408 A | 5/1991 | Reuss |
| 5,043,176 A | 8/1991 | Bycroft et al. |
| 5,069,286 A | 12/1991 | Roensch et al. |
| 5,084,239 A | 1/1992 | Moulton et al. |
| 5,093,140 A | 3/1992 | Watanabe |
| 5,114,178 A | 5/1992 | Baxter |
| 5,114,718 A | 5/1992 | Damani |
| 5,122,538 A | 6/1992 | Lokkesmoe et al. |
| 5,129,824 A | 7/1992 | Keller |
| 5,130,124 A | 7/1992 | Merianos et al. |
| 5,139,788 A | 8/1992 | Schmidt |
| 5,176,899 A | 1/1993 | Montgomery |
| 5,200,189 A | 4/1993 | Oakes et al. |
| 5,208,057 A | 5/1993 | Greenley et al. |
| 5,234,703 A | 8/1993 | Guthery |
| 5,234,719 A | 8/1993 | Richter et al. |
| 5,268,003 A | 12/1993 | Coope et al. |
| 5,292,447 A | 3/1994 | Venturello et al. |
| 5,314,687 A | 5/1994 | Oakes et al. |
| 5,336,500 A | 8/1994 | Richter et al. |
| 5,364,650 A | 11/1994 | Guthery |
| 5,391,324 A | 2/1995 | Reinhardt et al. |

(Continued)

FOREIGN PATENT DOCUMENTS

EP 0 195 619 A2 9/1986

(Continued)

OTHER PUBLICATIONS

Chemical Abstracts 134: 97683, 2000.*

(Continued)

*Primary Examiner*—John Pak
(74) *Attorney, Agent, or Firm*—Merchant & Gould P.C.

(57) ABSTRACT

The present invention relates to in situ compositions of mono- or diester dicarboxylates, methods employing these in situ compositions, and methods of making these in situ compositions. More particularly, the invention relates to mono- or diester dicarboxylate antimicrobial compositions that can reduce the population of microbes on various surfaces such as facilities, containers, or equipment found in food, beverage, or pharmaceutical processing, or in food, beverage, or pharmaceutical industries, at temperatures between about −70° C. to about 100° C.

31 Claims, No Drawings

U.S. PATENT DOCUMENTS

| | | | |
|---|---|---|---|
| 5,409,713 | A | 4/1995 | Lokkesmoe et al. |
| 5,419,908 | A | 5/1995 | Richter et al. |
| 5,435,808 | A | 7/1995 | Holzhauer et al. |
| 5,436,008 | A | 7/1995 | Richter et al. |
| 5,437,868 | A | 8/1995 | Oakes et al. |
| 5,489,434 | A | 2/1996 | Oakes et al. |
| 5,494,588 | A | 2/1996 | LaZonby |
| 5,508,046 | A | 4/1996 | Cosentino et al. |
| 5,512,309 | A | 4/1996 | Bender et al. |
| 5,527,898 | A | 6/1996 | Bauer et al. |
| 5,578,134 | A | 11/1996 | Lentsch et al. |
| 5,591,706 | A | 1/1997 | Ploumen |
| 5,595,967 | A | 1/1997 | Miracle et al. |
| 5,597,790 | A | 1/1997 | Thoen |
| 5,616,335 | A | 4/1997 | Nicolle et al. |
| 5,616,616 | A | 4/1997 | Hall et al. |
| 5,632,676 | A | 5/1997 | Kurschner et al. |
| 5,641,530 | A | 6/1997 | Chen |
| 5,656,302 | A | 8/1997 | Cosentino et al. |
| 5,658,467 | A | 8/1997 | LaZonby et al. |
| 5,674,538 | A | 10/1997 | Lokkesmoe et al. |
| 5,674,828 | A | 10/1997 | Knowlton et al. |
| 5,683,724 | A | 11/1997 | Hei et al. |
| 5,712,239 | A | 1/1998 | Knowlton et al. |
| 5,718,910 | A | 2/1998 | Oakes et al. |
| 5,756,139 | A | 5/1998 | Harvey et al. |
| 5,785,867 | A | 7/1998 | LaZonby et al. |
| 5,840,343 | A | 11/1998 | Hall et al. |
| 5,851,483 | A | 12/1998 | Nicolle et al. |
| 5,891,392 | A | 4/1999 | Monticello et al. |
| 5,900,256 | A | 5/1999 | Scoville, Jr. et al. |
| 5,902,619 | A | 5/1999 | Rubow et al. |
| 5,968,539 | A | 10/1999 | Beerse et al. |
| 5,989,611 | A | 11/1999 | Stemmler, Jr. et al. |
| 6,010,729 | A | 1/2000 | Gutzmann et al. |
| 6,024,986 | A | 2/2000 | Hei |
| 6,033,705 | A | 3/2000 | Isaacs |
| 6,049,002 | A | 4/2000 | Mattila et al. |
| 6,096,226 | A | 8/2000 | Fuchs et al. |
| 6,096,266 | A | 8/2000 | Duroselle |
| 6,096,348 | A | 8/2000 | Miner et al. |
| 6,207,108 | B1 | 3/2001 | Carr et al. |
| 6,593,283 | B1 * | 7/2003 | Hei et al. ................. 510/214 |

FOREIGN PATENT DOCUMENTS

| | | |
|---|---|---|
| EP | 0 233 731 A2 | 8/1987 |
| EP | 0 461 700 A1 | 12/1991 |
| EP | 0 569 066 A1 | 11/1993 |
| EP | 0 967 203 A1 | 12/1999 |
| EP | 1 061 071 A1 | 12/2000 |
| JP | 2086699 | 3/1990 |
| WO | WO 95/34537 | 12/1995 |
| WO | WO 98/28267 | 7/1998 |
| WO | WO 00/29038 | 5/2000 |
| WO | 00/30690 * | 6/2000 |

OTHER PUBLICATIONS

Classification Definitions, U.S. Patent Classification Definitions, Alexandria, VA, Dec. 2002, pp. 424-14 and 424-15, definition of "ORGANIC."*

Bell, K. et al., "Reduction of foodborne micro-organisms on beef carcass tissue using acetic acid, sodium bicarbonate, and hydrogen peroxide spray washes", *Food Microbiology*, vol. 14, pp. 439-448 (1997).

Eggensperger, H., "Disinfectants Based on Peracid-Splitting Compounds", *Zbl. Bakt. Hyg.*, I. Abt. Orig. B 168, pp. 51524 (1979).

Lion C. et al., "New decontaminants. Reaction of peroxyacid esters with toxic insecticides", *Bull. Soc. Chim. Belg.*, vol. 100, No. 7, pp. 555-559 (1991).

Merka, V. et al., "Disinfectant properties of some peroxide compounds.", Abstract No. 67542e, *Chemical Abstracts*, vol. 67 (1967).

Mulder, R.W.A.W. et al., "Research Note: Salmonella Decontamination of Broiler Carcasses with Lactic Acid, L-Cysteine, and Hdrogen Peroxide", *Poultry Science*, vol. 66, pp. 1555-1557 (1987).

Parker, W. et al., "Peroxides. II. Preparation, Characterization and Polarographic Behavior of Longchaing Aliphatic Peracids", *Synthesis and Properties of LongChain Aliphatic Peracids*, vol. 77, pp. 4037-4041 (Aug. 5, 1955).

Parker, W. et al., "Peroxides. IV. Aliphatic Diperacids", *Aliphatic Diperacids*, vol. 79, pp. 1929-1931 (Apr. 20, 1957).

Towle, G. et al., "Industrial Gums polysaccharides and Their Derivatives", Second Edition, Ch. XIX, "Pectin", pp. 429-444 (year unknown).

Armak Chemicals, "NEO-FAT Fatty Acids", *Akzo Chemicals Inc.*, Bulletin No. 86-17 (1986).

Computer search results—Level 1—5 patents (Mar. 1994).

Computer search results from Ecolab Information Center (Jun. 1998).

"Emery® Fatty and Dibasic Acids Specifications and Characteristics", *Emery Industries*, Bulletin 145, (Oct. 1983).

Pfizer Chemical Division, "Pfizer Flocon® Biopolymers for Industrial Uses (xanthan broths)", Data Sheet 679, pp. 1-4 (year unknown).

Copy of International Search Report dated Dec. 16, 2002.

* cited by examiner

IN SITU MONO-OR DIESTER DICARBOXYLATE COMPOSITIONS

FIELD OF THE INVENTION

The present invention relates to in situ compositions of mono- or diester dicarboxylates, methods employing these in situ compositions, and methods of making these in situ compositions. More particularly, the invention relates to mono- or diester dicarboxylate antimicrobial compositions that can reduce the population of microbes on various surfaces such as facilities, containers, or equipment found in food, beverage, or pharmaceutical processing, or in food, beverage, or pharmaceutical industries, at temperatures between about −70° C. to about 100° C.

BACKGROUND OF THE INVENTION

There has been a longstanding need for antimicrobial agents having improved antimicrobial efficacy and improved speed of action. The specific requirements for such agents vary according to the intended application (e.g., sanitizer, disinfectant, sterilant, aseptic packaging treatment, etc.) and the applicable public health requirements.

Many antimicrobial agents (e.g., iodophors, peracids, hypochlorites, chlorine dioxide, ozone, etc.) have a broad spectrum of antimicrobial properties. However, these agents sometimes have inadequate activity against bacterial spores, fungal spores, and fungi. Killing, inactivating, or otherwise reducing the active population of bacterial spores and fungi on surfaces is particularly difficult. Bacterial spores have a unique chemical composition of spore layers that make them more resistant than vegetative bacteria to the antimicrobial effects of chemical and physical agents. Likewise, the unique chemical composition of fungal cells, especially mold cells, makes them more resistant to chemical and physical agents than are other microorganisms. This resistance can be particularly troublesome when the spores or fungi are located on surfaces such as food, food contact sites, ware, hospitals and veterinary facilities, surgical implements, and hospital and surgical linens and garments.

The mold *Chaetomium funicola*, and bacterial spore-forming microorganisms of the *Bacillus* species are especially important to be aware of during food packaging, particularly during cold or hot aseptic filling of food and beverage, or pharmaceutical, products. Microorganisms of the *Bacillus* species include *Bacillus cereus, Bacillus mycoides, Bacillus subtilis, Bacillus anthracis,* and *Bacillus thuringiensis*. These latter microorganisms share many phenotypical properties, have a high level of chromosomal sequence similarity, and are known enterotoxin producers. *Bacillus cereus* is one of the most problematic because *Bacillus cereus* has been identified as possessing increased resistance to germicidal chemicals used to decontaminate environmental surfaces. For example, Blakistone et al., *Efficacy of Oxonia Active Against Selected Sporeformers*, Journal of Food Protection, Volume 62, pages 262–267, reported that *Bacillus cereus* was more tolerant to the effects of conventionally formulated peroxyacetic acid germicides than all other spore-forming bacteria tested, including other *Bacillus* and *Clostridium* species.

*Bacillus cereus* is frequently diagnosed as a cause of gastrointestinal disorders and has been suggested to be the cause of several food-borne illness outbreaks. Due to its rapid sporulating capacity, *Bacillus cereus* easily survives in the environment. *Bacillus cereus* is omnipresent in nature, and consequently can usually be found in animal feed and fodder. *Bacillus cereus* can contaminate raw milk via feces and soil, and can survive intestinal passage in cows and the pasteurization process. *Bacillus cereus* is also known to cause serious human illness via environmental contamination. For example, *Bacillus cereus* is known to cause post-traumatic injury eye infections, which can result in visual impairment or loss of vision within 12–48 hours after infection. In addition, *Bacillus cereus* is regarded as transferable from washed surgical garments to patients.

Agents having greater or faster activity against bacterial spores, fungi, and other resistant microorganisms (particularly microorganisms of the *Bacillus* species) could help meet a substantial public health need, and one that is not adequately addressed by current commonly-used antimicrobial agents.

SUMMARY OF THE INVENTION

The present invention relates to in situ compositions of mono- or diester dicarboxylates, methods employing these in situ compositions, and methods of making these in situ compositions. More particularly, the invention relates to mono- or diester dicarboxylate antimicrobial compositions that can reduce the population of microbes on various surfaces such as facilities, containers, or equipment found in food, beverage, or pharmaceutical processing, or in food, beverage, or pharmaceutical industries, at temperatures between about −70° C. to about 100° C. Typically the present compositions and methods are employed at temperatures from at or near ambient to about 70° C.

The in situ compositions of the present invention can include about 0.01 wt-% to about 95 wt-% mono- or diester dicarboxylate, 0.01 wt-% to about 90 wt-% hydrogen peroxide, 0 to about 5 wt-% stabilizer or catalyst, 0 to about 10 wt-% surfactant, 0 to about 10 wt-% buffer, and 0 to about 99.8 wt-% water. Preferred mono- or diester dicarboxylates include mono- or dimethyl, mono- or diethyl, mono- or dipropyl (n- or iso), or mono- or dibutyl esters (n-, sec, or tert), or amyl esters (n-, sec-, iso-, or tert-) of malonic, succinic, glutaric, adipic, or sebacic acids, or mixtures thereof. Mixed esters (e.g., monomethyl/monoethyl, or monopropyl/monoethyl) can also be employed. Preferred mono- or diester dicarboxylates are commercially available and soluble in water or another carrier at concentrations effective for antimicrobial activity. Preferred mono- or diester dicarboxylates are toxic to microbes but do not exhibit unacceptable toxicity to humans under formulation or use conditions.

The compositions of the invention can also include ingredients such as stabilizing agent, hydrotrope, coupling agent, surfactant, buffering agent, antioxidant, and the like. The compositions can be essentially free of added strong inorganic acids (e.g., sulfuric, phosphoric, nitric, hydrochloric, and the like).

In another embodiment, the present invention includes a method for making an antimicrobial in situ composition, particularly a use composition of an in situ composition of the invention. In an embodiment, this method includes adding hydrogen peroxide to a vessel, adding mono- or diester dicarboxylate to a vessel, or in reverse order, mixing the hydrogen peroxide and the mono- or diester dicarboxylate in the vessel. The method can also include adding a catalyst, stabilizer, or buffer, such as HEDP, phosphate, citrate/citric acid, bisulfate, borates, succinic acid, or a catalytic sulfonate-containing resin, or the like. The method further includes retaining the hydrogen peroxide and the mono- or diester dicarboxylate, and any other additives, in the vessel for a duration of from 0.05 minutes to no more than about 21 days (preferably from about 0.5 minutes to about 72 hours) to form the in situ composition of the present invention. For use, the method includes diluting the in situ composition to form a use antimicrobial composition. Optionally, to decrease the retention time, the method can include heating the in situ composition to between about 30° C. and about 100° C. and/or adding a catalyst.

Preferably, the method of making an in situ composition achieves a composition including about 1 wt-% to about 70 wt-% mono- or diester dicarboxylate, about 1 wt-% to about 50 wt-% hydrogen peroxide, about 0 to 2 wt-% stabilizer, or similar catalyst, 0 to 20 wt-% surfactants, 0 to about 10 wt-% buffering agent, with the balance being water.

This method can be carried out, for example, continuously, semi-continuously, or batch wise. Continuous formulation of an in situ concentrate or use composition removes composition and adds more ingredients as composition is removed. Preferably, for continuous formulation, adding mono- or diester dicarboxylate and aqueous hydrogen peroxide achieves a steady-state composition including about 0.1 wt-% to about 20 wt-% mono- or diester dicarboxylate, about 0.1 wt-% to about 20 wt-% hydrogen peroxide, optionally 0 to 2 wt-% stabilizer, 0 to about 10 wt-% surfactant, 0 to about 10 wt-% buffering agent, with the balance being water.

In another embodiment, the present invention includes a method for making and using a dilution of the in situ antimicrobial composition. Preferably, in this method, adding water or other diluting solvent or gas will yield a composition including Use compositions according to the present invention can include 0.01 wt-% to about 20 wt-% mono- or diester dicarboxylate, 0.01 wt-% to about 20 wt-% hydrogen peroxide, 0 to 2 wt-% stabilizer or catalyst, 0 to 5 wt-% surfactant, 0 to 5 wt-% buffer, with the balance being the diluting solvent. In a preferred embodiment, this composition is effective for reducing the population of one or more microorganisms on food packaging, such as aseptic food or beverage, or pharmaceutical, packaging.

In another embodiment, the invention includes a method employing an use composition of the in situ composition of the invention to reduce a population of one or more microorganisms on an object, such as a hard surface, soft surface, porous surface, food substance, or skin. These methods include contacting the object with an use composition of an in situ composition of the invention. Contacting can include spraying the composition, immersing the object in the composition, foam or gel treating the object with the composition, or a combination thereof. In an embodiment, the method includes contacting with use composition effective to reduce by more than 1-log order the population of spores and/or cells of Bacillus cereus and/or of Chaetomium funicola within 10 seconds at 60° C. In a preferred embodiment, this method reduces population of one or more microorganisms on food packaging, such as aseptic food or beverage, or pharmaceutical, packaging. In an embodiment, this method reduces population of one or more microorganisms on or in all or part of a beverage or food, or pharmaceutical, plant. In another embodiment, this method reduces population of microorganisms as a sterilant on surgical garments, equipment, surfaces, and the like.

In another embodiment, the present invention includes a method for cold aseptic bottling of beverages and foods, and pharmaceuticals, and waters. This method includes, for example, contacting a beverage or food container with an use composition of an in situ composition of the invention for sufficient period of time to reduce the microorganism population. In an embodiment, this method also includes rinsing the container, filling the container with a beverage or food, or pharmaceutical, and sealing the filled container. Typically, this method obtains a significantly reduced population of microorganisms resulting in a sanitized beverage or food, or pharmaceutical, container.

DETAILED DESCRIPTION OF THE INVENTION

Definitions

As used herein, the term "microorganism" refers to any noncellular or unicellular (including colonial) organism. Microorganisms include all prokaryotes. Microorganisms include bacteria (including cyanobacteria and Mycobacteria), lichens, microfungi, protozoa, virinos, viroids, viruses, and some algae. As used herein, the term "microbe" is synonymous with microorganism.

As used herein, the term "object" refers to a something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include a food product (and its surfaces); a body or stream of water or a gas (e.g., an air stream); and surfaces and articles employed in hospitality and industrial sectors.

As used herein, the phrase "food product" includes any food substance that might require treatment with an antimicrobial agent or composition and that is edible with or without further preparation. Food products include meat (e.g. red meat and pork), seafood, poultry, fruits and vegetables, eggs, living eggs, egg products, ready to eat food, wheat, seeds, roots, tubers, leafs, stems, corms, flowers, sprouts, seasonings, milk and milk products (e.g., yogurt, cheeses), teas, waters, or a combination thereof. The term "produce" refers to food products such as fruits and vegetables and plants or plant-derived materials that are typically sold uncooked, undercooked, or pasteurized, and, often, unpackaged, and that can sometimes be eaten raw (e.g., soy products, teas, yogurts, juices, dairy products).

As used herein, the phrase "dairy product" refers to all forms of food stuffs or beverages including or made from milk from any mammal. Dairy products include skim, reduced fat, and homogenized milk, cheese, yogurt, ice cream, frozen yogurt, sour cream, butter, and the like. Dairy products include cheese products, such as dips, spreads, snacks, and the like. Dairy products include sour cream products such as dips, spreads, and the like.

As used herein, the phrase "plant product" includes any plant substance or plant-derived substance that might require treatment with an antimicrobial agent or composition. Plant products include seeds, nuts, nut meats, cut flowers, plants or crops grown or stored in a greenhouse, house plants, and the like. Plant products include many animal feeds.

As used herein, a processed fruit or vegetable refers to a fruit or vegetable that has been cut, chopped, sliced, peeled, ground, milled, irradiated, frozen, cooked (e.g., blanched, pasteurized), or homogenized. As used herein a fruit or vegetable that has been washed, colored, waxed, hydrocooled, refrigerated, shelled, or had leaves, stems or husks removed is not processed.

As used herein, the phrase "meat product" refers to all forms of animal flesh, including the carcass, muscle, fat, organs, skin, bones and body fluids and like components that form the animal. Animal flesh includes the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein, the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "food processing surface" refers to a surface of a tool, a package or container, a wrap or film or covering, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, sanitizing gels, cooling towers, food processing antimicrobial garment sprays, and non-to-low-aqueous food preparation lubricants, oils, and rinse additives.

As used herein, the phrase "air streams" includes food anti-spoilage air circulation systems. Air streams also include air streams typically encountered in hospital, surgical, infirmity, birthing, mortuary, and clinical diagnosis rooms.

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and hand-wash dip-pans, third-sink rinse waters, and the like. Waters also include domestic and recreational waters such as pools, spas, recreational flumes and water slides, fountains, and the like.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.,), or woven and non-woven surfaces (such as surgical garments, draperies, bed linens, bandages, etc.,), or patient-care equipment (such as respirators, diagnostic equipment, shunts, body scopes, wheel chairs, beds, etc.,), or surgical and diagnostic equipment. Health care surfaces include articles and surfaces employed in animal health care.

As used herein, the term "instrument" refers to the various medical or dental instruments or devices that can benefit from cleaning with an in situ composition according to the present invention.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, arthoscopes and related equipment, and the like, or combinations thereof.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, weight percent (wt-%), percent by weight, % by weight, and the like are synonyms that refer to the concentration of a substance as the weight of that substance divided by the total weight of the composition and multiplied by 100.

As used herein, the terms "mixed" or "mixture" when used relating to "peroxycarboxylic acid composition" or "peroxycarboxylic acids" refer to a composition or mixture including more than one peroxycarboxylic acid, such as a composition or mixture including peroxyacetic acid and peroxyoctanoic acid.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

For the purpose of this patent application, successful reduction of microorganisms is achieved when the populations of microorganisms are reduced by at least about 0.3–1 $\log_{10}$. In this application, such a population reduction is the minimum acceptable for the processes.

Any increased reduction in population of microorganisms is an added benefit that provides higher levels of protection. For example, as set out in *Germicidal and Detergent Sanitizing Action of Disinfectants,* Official Methods of Analysis of the Association of Official Analytical Chemists, paragraph 960.09 and applicable sections, 15th Edition, 1990 (EPA Guideline 91-2), a sanitizer should provide a 99.999% reduction (5 log order reduction) within 30 seconds at room temperature, 25±2° C., against several test organisms.

As used herein, the term "sterilant" refers to a physical or chemical agent or process capable of destroying all forms of life (including bacteria, viruses, fungi, and spores) on inanimate surfaces. One procedure is described in *A. O. A. C. Sporicidal Activity of Disinfectants,* Official Methods of Analysis of the Association of Official Analytical Chemists, paragraph 966.04 and applicable sections, 15$^{th}$ Edition, 1990 (EPA Guideline 91-2)

As used herein, the term "antimicrobial composition" refers to a composition having the ability to cause greater than a 90% reduction (1-log order reduction) in the population of bacteria and/or spores of the *Bacillus* species within 10 seconds at 60° C. Preferably the *Bacillus* organism would be either *Bacillus cereus* or *Bacillus subtilis*.

Also preferably, the antimicrobial compositions of the invention provide greater than a 99% reduction (2 log order reduction), more preferably greater than a 99.99% reduction (4 log order reduction), and most preferably greater than a 99.999% reduction (5 log order reduction) in such composition within 10 seconds at 60° C. Preferably, the antimicrobial compositions of the invention also provide greater than a 99% reduction (2 log order reduction), more preferably greater than a 99.99% reduction (4 log order reduction), and most preferably greater than a 99.999% reduction (5 log order reduction) in the population of one or more additional organisms such as the mold *Chaetomium funicola*. Because in their broadest sense these definitions for antimicrobial activity are different from some of the current governmental regulations, the use in connection with this invention of the term "antimicrobial" is not intended to indicate compliance with any particular governmental standard for antimicrobial activity.

As used herein, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. Preferably, the sporicidal compositions of the invention provide greater than a 99% reduction (2 log order reduction), more preferably greater than a 99.99% reduction (4 log order reduction), and most preferably greater than a 99.999% reduction (5 log order reduction) in such population within 10 seconds at 60° C.

In Situ Mono- or Diester Dicarboxylate Antimicrobial Compositions

The present invention relates to in situ compositions containing a mono- or diester dicarboxylate. Typically, the in situ compositions include concentrations of mono- or diester dicarboxylate and hydrogen peroxide, plus any ester peroxycarboxylic acid that is formed by a reaction of the mono- or diester dicarboxylate with hydrogen peroxide. The in situ compositions can also include stabilizer, one or more additional antimicrobial agents, wetting agent, chelant, buffering agent, solvent (inert or antimicrobial), hydrotrope, surfactant, or mixtures thereof. The composition can be essentially free of strong inorganic acids (e.g., sulfuric, phosphoric, nitric, hydrochloric, and the like). Typically, the mono- or diester dicarboxylate and the ester peroxycarboxylic acid are antimicrobial agents.

Typical in situ compositions include about 0.01 wt-% to about 95 wt-% mono- or diester dicarboxylate, 0.01 wt-% to about 90 wt-% hydrogen peroxide, 0 to about 5 wt-% stabilizer or catalyst, 0 to about 10 wt-% surfactant, 0 to about 10 wt-% buffer, and 0 to about 99.8 wt-% water. Preferably, the in situ composition includes 0.05 wt-% to about 50 wt-% mono- or diester dicarboxylate, 0.05 wt-% to about 50 wt-% hydrogen peroxide, optionally 0 to about 5 wt-% stabilizer/catalyst (e.g. HEDP), 0 to about 10 wt-% surfactants, 0 to about 10 wt-% buffers, and 0 to about 95 wt-% added water. Preferably, the in situ composition includes about 0.1 wt-% to about 25 wt-% mono- or diester dicarboxylate, about 0.1 wt-% to about 30 wt-% hydrogen peroxide, optionally 0 to about 2 wt-% stabilizer/catalyst (e.g. HEDP), 0 to about 5 wt-% surfactants, 0 to about 5 wt-% buffers, and 0 to about 92 wt-% added water.

For example, the in situ composition can include about 10 wt-% mono- or diester dicarboxylate, about 10 wt-% hydrogen peroxide, and about 80 wt-% water plus optional additives. Preferably, the in situ composition can include about 5 wt-% mono- or diester dicarboxylate, about 10 wt-% hydrogen peroxide, and 85 wt-% water plus optional additives. Preferably the in situ composition can include about 2 wt-% mono- or diester dicarboxylate, about 5 wt-% hydrogen peroxide, and 97 wt-% water plus optional additives.

For example, the in situ composition can include about 0.1 wt-% to about 25 wt-% mono- or diester dicarboxylate, preferably about 1 wt-% to about 15 wt-% mono- or diester dicarboxylate, more preferably about 2 wt-% to about 10 wt-% mono- or diester dicarboxylate. For example, the in situ composition can include about 0.1 wt-% to about 30 wt-% hydrogen peroxide, preferably about 0.5 wt-% to about 20 wt-% hydrogen peroxide, more preferably about 1 wt-% to about 10 wt-% hydrogen peroxide. For example, the in situ composition can include 0 to about 10 wt-% stabilizer, preferably 0 to about 5 wt-% stabilizer, more preferably 0 to about 2 wt-% stabilizer. For example, the in situ composition can include 0 to about 10 wt-% buffering agents, preferably 0 to about 5 wt-% buffering agents, more preferably 0 to about 2 wt-% buffering agents. For example, the in situ composition can include 0 to about 99.8 wt-% water, preferably 0 to about 95 wt-% water, more preferably 0 to about 90 wt-% water.

These preferred in situ compositions can be used as is or mixed with a diluting solvent or gas that will yield a use composition including 0.01 wt-% to about 20 wt-%, preferably 0.1 wt-% to about 10 wt-%, and more preferably 0.5 wt-% to about 7 wt-% mono- or diester dicarboxylate; 0.01 wt-% to about 20 wt-%, preferably 0.5 wt-% to about 12 wt-%, and more preferably 0.5 wt-% to about 7 wt-%, hydrogen peroxide; optionally 0 to 2 wt-%, preferably 0 to about 1 wt-%, and more preferably 0 to about 0.5 wt-% stabilizer or catalyst; optionally 0 to 5 wt-%, preferably 0 to about 2 wt-%, and more preferably 0 to about 1 wt-% surfactant, 0 to 5 wt-%, preferably 0 to about 2 wt-%, and more preferably 0 to about 1 wt-% buffers; with the balance being the diluting solvent.

In a preferred embodiment, this composition reduces the population of one or more microorganisms on food packaging, such as aseptic food or beverage, or pharmaceutical, packaging.

The present in situ mono- or diester dicarboxylate compositions can include components such as stabilizers, particularly those suitable for stabilizing peroxygen or peracid (peroxyacid, esterperacid). The type and breadth of stabilizers suitable for this purpose is well-known in the art. Such stabilizers include organic chelating compounds that sequester metal ions in solution, particularly most transition metal ions, which would promote decomposition of any peroxygen compounds therein. Typical complexing agents include organic amino- or hydroxy-polyphosphonic acid complexing agents (either in acid or soluble salt forms), carboxylic acids, hydroxycarboxylic acids, or aminocarboxylic acids. Example stabilizers expressed in acid form include dipicolinic acid, picolinic acid, gluconic acid, quinolinic acid, and ethylenediarnine tetraacetic acid (EDTA). Preferred stabilizers include phosphonates such as: hydroxyethylene diphosphonic acid (HEDP), ethylenediamine tetrakis methylenephosphonic acid (EDTMP), diethylenetriamine pentakis methylenephosphonic acid (DTPMP), and cyclohexane-1,2-tetramethylene phosphonic acid. The concentration of stabilizer is typically 0 to about 5 wt-% in the composition.

Preferably, the in situ composition of the invention does not include any added strong inorganic acid (e.g., sulfuric, phosphoric, nitric, hydrochloric, and the like). That is, the in situ composition of the invention preferably does not include a strong mineral acid, except for any incidental amounts that might be present in the mono- or diester dicarboxylate, the hydrogen peroxide, the water, or any additional ingredients, e.g. the stabilizing agent. The in situ composition of the present invention can include any acid that results from reaction between the mono- or diester dicarboxylate, the hydrogen peroxide, the water, the buffering agent, and any additional ingredient (e.g., stabilizing agent) that might be present in the composition. Such in situ compositions can be denoted as free of added strong inorganic acid.

Ester peroxycarboxylic acid, mono- or diester dicarboxylate, hydrogen peroxide, and water can be involved in a reaction in the in situ composition of the invention. One reaction converts the mono- or diester dicarboxylate to the corresponding monoester peroxy dicarboxylic acid and/or peroxy dicarboxylic acid. The compositions and methods of the present invention include compositions that, upon reacting, yield in situ ester peroxycarboxylic acid compositions.

The in situ mono- or diester dicarboxylate composition can also include one or more adjuvants, such as solvents, cosolvents, surfactants, hydrotropes, buffering agents, chelants, stabilizers, catalysts, thickening agents, aerosolizing agents, and the like.

Diester Dicarboxylates

As used herein, diester dicarboxylates refer to molecules having the formula:

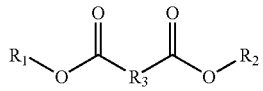

In this formula, $R_1$, $R_2$, and $R_3$ can independently be any of a wide variety of organic groups (e.g. alkyl, linear or cyclic, aromatic or saturated) or substituted organic groups (e.g., with one or more heteroatoms or organic groups). Diester dicarboxylates, or monoester dicarboxylates (disclosed later) can be converted to ester peroxycarboxylic acids, for example, by incubating the corresponding mono- or diester dicarboxylate with hydrogen peroxide.

Preferred diester dicarboxylates include alkyl diester dicarboxylates, preferably having the formula:

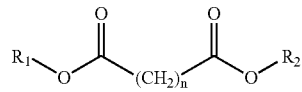

where $R_1$ and $R_2$ represent independently an alkyl group having from 1 to 8 carbons, preferably 1 to 5, and n is 0 to 6, preferably 1 to 5. The alkyl group can be either straight chain or branched. Preferably, $R_1$ and $R_2$ are independently a methyl, ethyl, propyl (n-, iso-), butyl (n-, iso-, tert-), n-amyl, n-hexyl, or 2-ethylhexyl group. Preferably, n is 2, 3, 4, or 5. In one preferred embodiment, the composition of the present invention includes a mixture of alkyl diester dicarboxylates in which x is 2, 3, and 4. Such a mixture includes diesters of peroxyadipic, peroxyglutaric, and peroxysuccinic acids. In another preferred embodiment, a majority of the alkyl diester dicarboxylates in the composition has n equal to 3 or 4. In yet another preferred embodiment, a majority of the alkyl diester dicarboxylates in the composition has n equal to 5. In a preferred embodiment, $R_1$ and $R_2$ are independently a $C_1$–$C_8$ alkyl. In a preferred embodiment, n is 1, 2, 3, or 4. Most preferably, $R_1$ and $R_2$ are independently a $C_1$ alkyl, $C_3$ alkyl, $C_4$ alkyl, and n is 2, 3 4, or 5. In another preferred embodiment, $R_1$ and $R_2$ are independently a $C_5$–$C_8$ alkyl, n is 5 or 6.

Alkyl diester dicarboxylates useful in this invention include all symmetrical and mixed diesters of oxalic acid, malonic acid, succinic acid, glutaric acid, adipic acid, or sebacic acid (or mixtures thereof) with methanol, ethanol, propanol (e.g., n-propanol or isopropanol), butanol (e.g., n-butanol, iso-butanol, or tert-butanol), amyl alcohol (n-pentanol, iso-pentanol, sec-pentanol, or tert-pentanol), hexanol (n-hexanol, iso-hexanol, sec-hexanol, or tert-hexanol), octanol (n-octanol, iso-octanol, sec-octanol, or tert-octanol) or mixtures thereof. Such alkyl diester dicarboxylates include dimethyl oxalate, methyl ethyl oxalate, methyl propyl oxalate, methyl butyl oxalate, dimethyl malonate, methyl ethyl malonate, methyl propyl malonate, methyl butyl malonate, dimethyl succinate, methyl ethyl succinate, methyl propyl succinate, methyl butyl succinate, dimethyl glutarate, methyl ethyl glutarate, methyl propyl glutarate, methyl butyl glutarate, dimethyl adipate, methyl ethyl adipate, methyl propyl adipate, methyl butyl adipate, dimethyl sebacate, methyl ethyl sebacate, methyl propyl sebacate, methyl butyl sebacate, diethyl oxalate, ethyl propyl oxalate, ethyl butyl oxalate, diethyl malonate, ethyl propyl malonate, ethyl butyl malonate, diethyl succinate, ethyl propyl succinate, ethyl butyl succinate, diethyl glutarate, ethyl propyl glutarate, ethyl butyl glutarate, diethyl adipate, ethyl propyl adipate, ethyl butyl adipate, diethyl sebacate, ethyl propyl sebacate, ethyl butyl sebacate, dipropyl oxalate, propyl butyl oxalate, dipropyl malonate, propyl butyl malonate, dipropyl succinate, propyl butyl succinate, dipropyl glutarate, propyl butyl glutarate, dipropyl adipate, propyl butyl adipate, dipropyl sebacate, propyl butyl sebacate, dibutyl oxalate, dibutyl malonate, dibutyl succinate, dibutyl glutarate, dibutyl adipate, dibutyl sebacate, diamyl succinate, diamyl glutarate, diamyl adipate, diamyl sebacate, dihexyl succinate, dihexyl glutarate, dihexyl adipate, dihexyl sebacate, diethylhexyl succinate, diethylhexyl glutarate, diethylhexyl adipate, diethylhexyl sebacate, or mixtures thereof. In these esters propyl can be n- or iso-propyl; butyl can be n-, iso-, or tert-butyl; amyl can be n-, sec-, iso-, tert-amyl; hexyl can be n-, sec-, iso-, tert-hexyl; and octyl can be n-, iso-, sec-, tert-octyl, or 2-ethylhexyl-, or a mixture thereof.

The methods and compositions of the present invention can also include diester dicarboxylates known as dibasic esters and available under the trade designations DBE, DBE-3, DBE-4, DBE-5, DBE-6, DBE-9, DBE-IB, and DBE-ME from DuPont Nylon. These "DBEs" include single isolates or mixtures of species such as dimethyl adipate, dimethyl succinate, dimethyl glutarate, and diisobutyl adipate, diisobutyl succinate, and diisobutyl glutarate. Other diester dicarboxylates, such as dioctyl sebacate, bis-[2-ethylhexyl] sebacate, diamyl sebacate, are also commercially available in relatively pure form. These DBEs and the sebacate esters are preferred, in part, since they are commercially and economically available. Additional suitable diester dicarboxylates (or dibasic esters) include dimethyl malonate, dimethyl sebacate, diethyl adipate, diethyl succinate, diethyl glutarate, dibutyl succinate, and dibutyl glutarate; dialkyl carbonates such as dimethyl carbonate, diethyl carbonate, dipropyl carbonate, diisopropyl carbonate, and dibutyl carbonate.

Ester Peroxycarboxylic Acids

As used herein, ester peroxycarboxylic acid refers to a molecule having the formula:

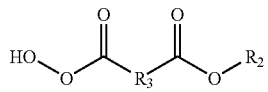

In this formula, $R_2$ and $R_3$ can independently be any of a wide variety of organic groups (e.g. alkyl, linear or cyclic, aromatic or saturated) or substituted organic groups (e.g., with one or more heteroatoms or organic groups). Ester peroxycarboxylic acid can be made using methods typically employed for producing peroxycarboxylic acid, such as incubating the corresponding monoester (described later) or diester (previously described) dicarboxylate with hydrogen peroxide. Ester peroxycarboxylic acids derived from or corresponding to the mono- or diester dicarboxylates described herein are preferred.

Preferred ester peroxycarboxylic acids include alkyl ester peroxycarboxylic acids, preferably having the formula:

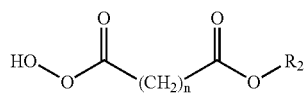

where $R_2$ represents an alkyl group having from 1 to 8 carbons and n is 0 to 6, preferably 1 to 5. The alkyl group can be either straight chain or branched. Preferably, $R_2$ is a methyl, ethyl, propyl (n-, iso-), butyl (n-, iso-, tert-), n-amyl, n-hexyl, or 2-ethylhexyl group. Preferably, n is 2, 3, 4, or 5.

In one preferred embodiment, the composition of the present invention includes a mixture of alkyl ester peroxycarboxylic acids in which n is 2, 3, and 4. Such a mixture includes monoesters of peroxyadipic, peroxyglutaric, and peroxysuccinic acids. In another preferred embodiment, a majority of the ester peroxycarboxylic acid in the composition has x equal to 3. In a preferred embodiment, $R_2$ is a $C_1$–$C_8$ alkyl. In a preferred embodiment, n is 1, 2, 3, or 4. Most preferably, $R_2$ is a $C_1$ alkyl, $C_2$ alkyl, $C_3$ alkyl, or $C_4$ alkyl, and n is 2, 3 or 4, or a combination thereof. In another most preferred embodiment, R2 is a $C_5$–$C_8$ alkyl, n is 5 or 6.

Alkyl ester peroxycarboxylic acids usefuil in this invention include monomethyl monoperoxyoxalic acid, monomethyl monoperoxymalonic acid, monomethyl monoperoxysuccinic acid, monomethyl monoperoxyglutaric acid, monomethyl monoperoxyadipic acid, monomethyl monoperoxysebacic acid; monoethyl monoperoxyoxalic acid, monoethyl monoperoxymalonic acid, monoethyl Imonoperoxysuccinic acid, monoethyl monoperoxyglutaric acid, monoethyl monoperoxyadipic acid, monoethyl monoperoxysebacic acid; monopropyl monoperoxyoxalic acid, monopropyl monoperoxymalonic acid, monopropyl monoperoxysuccinic acid, monopropyl monoperoxyglutaric acid, monopropyl monoperoxyadipic acid, monopropyl monoperoxysebacic acid, in which propyl can be n- or iso-propyl; monobutyl monoperoxyoxalic acid, monobutyl monoperoxymalonic acid, monobutyl monoperoxysuccinic acid, monobutyl monoperoxyglutaric acid, monobutyl monoperoxyadipic acid, monobutyl monoperoxysebacic acid, in which butyl can be n-, iso-, or t-butyl; monoamyl monoperoxyoxalic acid, monoamyl monoperoxymalonic acid, monoamyl monoperoxysuccinic acid, monoamyl monoperoxyglutaric acid, monoamyl monoperoxyadipic acid, monoamyl monoperoxysebacic acid, in which amyl is n-; monohexyl monoperoxysebacic acid, in which hexyl is n-; mono-2-ethylhexyl monoperoxysebacic acid.

Peroxycarboxylic Acid Antimicrobial Compositions

Compositions of Carboxylic Acids and Peroxycarboxylic Acids

Among other constituents, the composition of the present invention includes a carboxylic acid. Generally, carboxylic acids have the formula R—COOH wherein the R can represent any number of different groups including aliphatic groups, alicyclic groups, aromatic groups, heterocyclic groups, and ester groups, such as alkyl ester groups, all of which can be saturated or unsaturated and/or substituted or unsubstituted. Preferably R is a small alkyl group with 1–10 carbons, most preferably 1–8 carbons.

Carboxylic acids can have one, two, three, or more carboxyl groups. Preferred ester groups include aliphatic ester groups, such as $R_1OC(O)R_2$— where each of $R_1$ and $R_2$ can be aliphatic, preferably alkyl, groups described above for R. Preferably $R_1$ and $R_2$ are each independently small alkyl groups, such as alkyl groups with 1 to 8, most preferably 1 to 5, carbon atoms. Examples of suitable alkyl ester carboxylic acids include monomethyl oxalic acid, monomethyl malonic acid, monomethyl succinic acid, monomethyl glutaric acid, monomethyl adipic acid, monomethyl sebacic acid; monoethyl oxalic acid, monoethyl malonic acid, monoethyl succinic acid, monoethyl glutaric acid, monoethyl adipic acid, monoethyl sebacic acid; monopropyl oxalic acid, monopropyl malonic acid, monopropyl succinic acid, monopropyl glutaric acid, monopropyl adipic acid, monopropyl sebacic acid, in which propyl can be n- or isopropyl; monobutyl oxalic acid, monobutyl malonic acid, monobutyl succinic acid, monobutyl glutaric acid, monobutyl adipic acid, monobutyl sebacic acid, in which butyl can be n-, iso-, or t-butyl; monoamyl oxalic acid, monoamyl malonic acid, monoamyl succinic acid, monoamyl glutaric acid, monoamyl adipic acid, monoamyl sebacic acid, in which amyl is n-; monohexyl sebacic acid, in which hexyl is n-; and mono-2-ethylhexyl sebacic acid.

Carboxylic acids which are generally useful are those having one or two carboxyl groups where the R group is a primary alkyl or aryl chain having a length of $C_2$ to $C_{12}$. The primary alkyl or aryl chain is that carbon chain of the molecule having the greatest length of carbon atoms and directly appending carboxyl functional groups. Examples of suitable carboxylic acids include acetic acid, propionic acid, hexanoic acid, heptanoic acid, octanoic acid, nonanoic acid, decanoic acid, benzoic acid, salicylic acid, and mixtures thereof. Longer chain carboxylic acid analogues, including hexanoic, heptanoic, octanoic, nonanoic, and decanoic, can be additionally antimicrobial and reduce surface tension to assist in wetting of hydrophobic surfaces like skin.

Other carboxylic acids that are generally useful include ester carboxylic acids, such as alkyl ester carboxylic acids. These monoester dicarboxylates can be utilized in conjunction with the current compositions or they can be converted to ester peroxycarboxylic acids, for example, by incubating the corresponding monoester dicarboxylate with hydrogen peroxide. Preferred alkyl ester carboxylic acids include those with the formula:

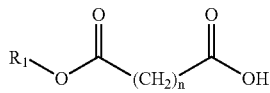

where $R_1$ represents an alkyl group having from 1 to 8 carbons and n is 0 to 6, preferably 1 to 5. The alkyl group can be either straight chain or branched. Preferably, $R_1$ is a methyl, ethyl, propyl (n-, iso-), butyl (n-, iso-tert-), n-amyl, n-hexyl, or 2-ethylhexyl group. Preferably, n is 2, 3, or 4. In one preferred embodiment, the composition of the present invention includes a mixture of alkyl ester peroxycarboxylic acids in which n is 2, 3, and 4. Such a mixture includes monoesters of peroxyadipic, peroxyglutaric, and peroxysuccinic acids. In another preferred embodiment, a majority of the ester peroxycarboxylic acid in the composition has n equal to 3. In a preferred embodiment, $R_1$ is a $C_1$–$C_4$ alkyl. In a preferred embodiment, n is 1, 2, 3, or 4. Most preferably, $R_1$ is a $C_1$ alkyl, $C_3$ alkyl, or $C_4$ alkyl, and n is 2, 3 or 4. In another preferred embodiment, $R_1$ is a $C_5$–$C_8$ alkyl, n is 5 or 6.

Suitable mono- or diester carboxylates for use in these in situ compositions include any of those described herein below. Preferred mono-dicarboxylates for in situ compositions of the present invention include the mono-ester dicarboxylic acids such as monomethyl oxalic acid, monomethyl malonic acid, monomethyl succinic acid, monomethyl glutaric acid, monomethyl adipic acid, monomethyl sebacic acid; monoethyl oxalic acid, monoethyl malonic acid, monoethyl succinic acid, monoethyl glutaric acid, monoethyl adipic acid, monoethyl sebacic acid; monopropyl oxalic acid, monopropyl malonic acid, monopropyl succinic acid, monopropyl glutaric acid, monopropyl adipic acid, monopropyl sebacic acid (n-, iso-), monobutyl oxalic acid, monobutyl malonic acid, monobutyl succinic acid, monobutyl glutaric acid, monobutyl adipic acid, monobutyl sebacic acid (n-, iso-, or tert-), monoamyl oxalic acid, monoamyl malonic acid, monoamyl succinic acid, monoamyl glutaric acid, monoamyl adipic acid, monoamyl sebacic acid (n-, iso-, sec-, or tert-), monohexyl oxalic acid, monohexyl malonic acid, monohexyl succinic acid, monohexyl glutaric acid, monohexyl adipic acid, monohexyl sebacic acid (n-, iso-, sec-, or tert-) monooctyl oxalic acid, monooctyl malonic acid, monooctyl succinic acid, monooctyl glutaric acid, monooctyl adipic acid, monooctyl sebacic acid (n-, iso-, sec-, 2-ethylhexyl-, or tert-).

Peroxycarboxylic (or percarboxylic) acids generally have the formula $R(CO_3H)_n$, where R is an alkyl, arylalkyl, cycloalkyl, aromatic, heterocyclic, or ester group, such as an alkyl ester group; and n is one, two, or three, and named by prefixing the parent acid with peroxy. Ester groups are defined as R groups including organic moieties (such as those listed above for R) and ester moieties. Preferred ester groups include aliphatic ester groups, such as $R_1OC(O)R_2$— where each of $R_1$ and $R_2$ can be aliphatic, preferably alkyl, groups described above for R. Preferably $R_1$ and $R_2$ are each independently small alkyl groups, such as alkyl groups with 1 to 8 carbon atoms.

While peroxycarboxylic acids are not as stable as carboxylic acids, their stability generally increases with increasing molecular weight. Thermal decomposition of these acids can generally proceed by free radical and non-radical paths, by photodecomposition or radical-induced decomposition, or by the action of metal ions or complexes. Percarboxylic acids can be made by the direct, acid catalyzed equilibrium action of hydrogen peroxide with the carboxylic acid, by autoxidation of aldehydes, or from acid chlorides, and hydrides, or carboxylic anhydrides with hydrogen or sodium peroxide.

Peroxycarboxylic acids useful in the compositions and methods of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, peroxylactic, peroxycitric, peroxymaleic, peroxyascorbic, peroxyhydroxyacetic (peroxyglycolic), peroxyoxalic, peroxymalonic, peroxysuccinic, peroxyglutaric, peroxyadipic, peroxypimelic and peroxysubric acid and mixtures thereof. Useful peroxycarboxylic acids also include the ester peroxycarboxylic acids described herein above and compositions of the present invention including those ester peroxycarboxylic acids.

Peroxy forms of carboxylic acids with more than one carboxylate moiety can have one or more of the carboxyl moieties present as peroxycarboxyl moieties. These peroxycarboxylic acids have been found to provide good antimicrobial action with good stability in aqueous mixtures. In a preferred embodiment, the composition of the invention utilizes a combination of several different peroxycarboxylic acids.

In preferred embodiment, the antimicrobial composition includes one or more alkyl ester peroxycarboxylic acids and, optionally, a peroxycarboxylic acid having from 2 to 12 carbon atoms. Preferably, such an antimicrobial composition includes peroxyacetic acid, or peroxyoctanoic acid, or peroxydecanoic acid, and monomethyl monoperoxyoxalic acid, monomethyl monoperoxymalonic acid, monomethyl monoperoxysuccinic acid, monomethyl monoperoxyglutaric acid, monomethyl monoperoxyadipic acid; monoethyl monoperoxyoxalic acid, monoethyl monoperoxymalonic acid, monoethyl monoperoxysuccinic acid, monoethyl monoperoxyglutaric acid, monoethyl monoperoxyadipic acid; monopropyl monoperoxyoxalic acid, monopropyl monoperoxymalonic acid, monopropyl monoperoxysuccinic acid, monopropyl monoperoxyglutaric acid, monopropyl monoperoxyadipic acid, in which propyl can be n- or isopropyl; monobutyl monoperoxyoxalic acid, monobutyl monoperoxymalonic acid, monobutyl monoperoxysuccinic acid, monobutyl monoperoxyglutaric acid, monobutyl monoperoxyadipic acid, in which butyl can be n-, iso-, or tert-butyl; monoamyl oxalic acid, monoamyl malonic acid, monoamyl succinic acid, monoamyl glutaric acid, monoamyl adipic acid, monoamyl sebacic acid, in which amyl is n-; monohexyl sebacic acid, in which hexyl is n-; and mono-2-ethylhexyl sebacic acid, or mixtures thereof.

The amount of alkyl ester peroxycarboxylic acid in use and concentrate compositions can range up to the limits at which the peroxycarboxylic acid can be dissolved or suspended in the composition. Preferably, the peroxycarboxylic acid or alkyl ester peroxycarboxylic acid are, independently, present in concentrate compositions at concentrations of from about 0.01 to about 30% by weight, preferably from 0.05 to about 18% by weight, and more preferably from about 0.5 to about 10% by weight. Typically use solutions of the above concentrate compositions include, independently, the peroxycarboxylic acid or alkyl ester peroxycarboxylic acid at concentrations of from 0.0001 to about 5% by weight, preferably from 0.01 to about 3% by weight, and more preferably from about 0.1 to about 2% by weight.

A preferred antimicrobial in situ mono- or diester dicarboxylate composition or in situ ester peroxycarboxylic acid composition of the present invention is effective for killing one or more of the pathogenic or contaminating spore-forming bacteria or fungi associated with foods, beverages, pharmaceuticals, or their packaging or containers. Such fungi or bacteria include *Zygosaccharomyces bailii, Bacillus cereus, Bacillus subtilis*, and molds including *Chaetomium* spp., e.g., *Chaetomium funicola, Arthrinium,* and like genera; yeast, other molds, and the like. The compositions and methods of the present invention have activity against a wide variety of microorganisms such as Gram positive (for example, *Listeria monocytogenes*) and Gram negative (for example, *Escherichia coli*) bacteria, yeast, molds, bacterial spores, viruses, etc. The compositions and methods of the present invention, as described above, have activity against a wide variety of human pathogens including *Staphylococcus aureus, Pseudomonas aeruginosa*. The compositions and methods can kill a wide variety of microorganisms on a food, beverage, or pharmaceutical processing surface or equipment.

A preferred antimicrobial in situ mono- or diester dicarboxylate composition or in situ ester peroxycarboxylic acid composition of the present invention is effective for killing one or more of the food-borne pathogenic bacteria associated with a food product, such as *Salmonella typhimurium, Salmonella javiana, Campylobacter jejuni, Listeria monocytogenes,* and *Escherichia coli* O157:H7, yeast, mold and the like. The compositions and methods of the present invention, as described above, have activity against a wide variety of human pathogens. The compositions and methods can kill a wide variety of microorganisms on a food processing surface, on the surface of a food product, or in water used for washing or processing of food product.

The compositions and methods are also useful against a wide variety of microorganisms on a health care surface or in a health care environment.

The preferred compositions include concentrate compositions and use compositions. Typically, an antimicrobial concentrate composition can be diluted with a solvent, gas, or steam, for example with water, to form an antimicrobial use composition. In a preferred embodiment, the concentrate composition is diluted into water employed for washing or processing a food, beverage, or pharmaceutical, or a container or equipment employed in producing foods, beverages, or pharmaceuticals, or for filling food or beverage or pharmaceutical containers.

The advantageous stability of in situ mono- or diester dicarboxylate compositions or in situ peroxycarboxylic acid compositions in such methods, makes these compositions competitive with cheaper, less stable, and potentially toxic chlorinated compounds. Preferred methods of the present invention include agitation, aspiration, pumping, fogging, or sonication of the use composition, particularly as a concentrate is added to water to make the use composition. Preferred methods include water systems that have some agitation, spraying, fogging, re-circulation, or other mixing of the solution.

The level of reactive species, such as peroxy acids and/or hydrogen peroxide, in a use composition can be affected, typically diminished, by organic matter that is found in or added to the use composition. Thus, the amounts of ingredients listed for the use compositions refer to the composition before or early in use, with the understanding that the amounts will diminish as organic matter is added to the use composition.

Hydrogen Peroxide

The in situ compositions of the invention typically also include a hydrogen peroxide constituent. Hydrogen peroxide in combination with the percarboxylic acid provides certain biofilm removal or antimicrobial action against microorganisms. Additionally, hydrogen peroxide can provide an effervescent action which can irrigate any surface to which it is applied. Hydrogen peroxide works with a mechanical flushing action once applied which further cleans the surface. An additional advantage of hydrogen peroxide is the food compatibility of this composition upon use and decomposition. For example, combinations of peroxyacetic acid, peroxyoctanoic acid, and hydrogen peroxide result in acetic acid, octanoic acid, water, and oxygen upon decomposition, all of which are food product compatible.

Many oxidizing agents can be used for generating peroxycarboxylic acids. Suitable oxidizing agents, in addition to hydrogen peroxide, include salts of perborate, percarbonate, and persulfate, percarbonic acid, and ozone. Hydrogen peroxide is generally preferred for several reasons. After application of the $H_2O_2$/peroxycarboxylic acid germicidal agent, the residue left merely includes water and an acidic constituent. Deposition of these products on the surface of a food product processing apparatus, such as a bath or spray apparatus, will not adversely effect the apparatus, the handling or processing, or the food product washed therein.

Solvent

A variety of solvents can be employed in the compositions and methods of the present invention. In general, the solvent is selected based upon characteristics of the selected mono- or diester dicarboxylate and other additives. Water is the most preferred solvent. Other suitable solvents include densified gases such as carbon dioxide or organic solvents such as amyl acetate, amyl alcohol, or $C_1$ or greater alkyl alcohols. Such alcohols may be linear or branched and contain mixtures of alcohols. The alcohols may be monohydric, dihydric or polyhydric.

Other solvents can be useful as antimicrobial synergistic agents in the compositions. Such antimicrobial solvents include acetamidophenol, acetanilide, acetophenone, 2-acetyl-1-methylpyrrole, benzyl acetate, benzyl alcohol, benzyl benzoate, benzyloxyethanol, ethers or hydroxyethers such as ethylene glycol phenyl ether, and propylene glycol phenyl ether; essential oils (e.g., benzaldehyde, pinenes, terpineols, terpinenes, carvone, cinnamealdehyde, borneol and its esters, citrals, ionenes, jasmine oil, limonene, dipentene, linalool and its esters); dibasic esters such as dimethyl adipate, dimethyl succinate, dimethyl glutarate, including products available under the trade designations DBE, DBE-3, DBE-4, DBE-5, DBE-6, DBE-9, DBE-IB, and DBE-ME from DuPont Nylon), dimethyl malonate, diethyl adipate, diethyl succinate, diethyl glutarate, dibutyl succinate, and dibutyl glutarate; dialkyl carbonates such as dimethyl carbonate, diethyl carbonate, dipropyl carbonate, diisopropyl carbonate, and dibutyl carbonate; $C_{1-16}$ protonated carboxylic acids such as 2-ethyl-1-hexanoic acid, butyric acid, octanoic acid, heptanoic acid, nonanoic acid, and decanoic acid; $C_{1-12}$ organic anhydrides such as acetic anhydride, succinic anhydride, phthalic anhydride, maleic anhydride, and alkyl or alkenyl succinic anhydrides; organo-nitriles such as benzonitrile; organo-phosphates and phosphonates such as tributyl phosphate, tripropyl phosphate, 2-ethyl-1-hexyl phosphate; and phthalate esters such as dibutyl phthalate, diethylhexyl phthalate, and diethyl phthalate. Benzyl alcohol, phenylethanol, essential oils, dibasic esters, dialkyl carbonates, ethylene glycol phenyl ether and propylene glycol phenyl ether are preferred antimicrobially-active solvents.

Mixtures of antimicrobially-active solvents can be used if desired. Water, as a solvent, can be added at a concentration of about 0 to about 99 wt-%. Inert or antimicrobially active organic solvents are preferably present at a concentration of about 0 to about 99 wt-%, preferably about 0 to about 25 wt-%, more preferably about 0 to about 15 wt-%. A most preferred solvent would be compatible as an indirect or direct food additive or substance; especially those described in the Code of Federal Regulations (CFR), Title 21—Food and Drugs, parts 170 to 186 (which is incorporated herein by reference).

Cosolvent

A variety of cosolvents can be employed. In general, the cosolvent is selected based upon characteristics of the selected mono- or diester dicarboxylate, such as its solubility in the diluting solvent. For compositions in which water serves as the diluting solvent, the cosolvent generally will have higher water solubility than the water solubility of the selected mono- or diester dicarboxylate. Preferably, the cosolvent has a flashpoint greater than about 30° C., more preferably greater than about 50° C., and most preferably greater than about 100° C.; low odor; and low human and animal toxicity.

Preferred cosolvents are such as amyl acetate, amyl alcohol, butanol, 3-butoxyethyl-2-propanol, butyl acetate, n-butyl propionate, cyclohexanone, diacetone alcohol, diethoxyethanol, diethylene glycol methyl ether, diethylene glycol n-butyl ether, diisobutyl carbinol, diisobutyl ketone, dimethyl heptanol, dipropylene glycol n-butyl ether, dipropylene glycol methyl ether, dipropylene glycol propyl ether, dipropylene glycol tert-butyl ether, ethanol, ethyl acetate, 2-ethylhexanol, ethyl propionate, ethylene glycol butyl ether, ethylene glycol methyl ether acetate, hexanol, isobutanol, isobutyl acetate, isobutyl heptyl ketone, isophorone, isopropanol, isopropyl acetate, methanol, methyl amyl alcohol, methyl n-amyl ketone, 2-methyl-1-butanol, methyl ethyl ketone, methyl isobutyl ketone, 1-pentanol, n-pentyl propionate, 1-propanol, n-propyl acetate, n-propyl propionate, propylene glycol n-butyl ether, propylene glycol ethyl ether, propylene glycol methyl ether, propylene glycol n-propyl ether, tripropylene glycol methyl ether and tripropylene glycol n-butyl ether. Ethylene glycol butyl ether and dipropylene glycol n-butyl ether are preferred cosolvents. Mixtures of cosolvents can be used if desired.

Commercially available cosolvents (all of which are available from Union Carbide Corp.) include Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™, FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™, Methyl PROPASOL™ acetate, Methyl PROPASOL™, Propyl CARBITOL™, Propyl CELLOSOLVE™, Propyl DIPROPASOL™ and Propyl PROPASOL™.

A more preferred co-solvent would be compatible as an indirect or direct food additive or substance; especially those described in the Code of Federal Regulations (CFR), Title 21—Food and Drugs, parts 170 to 186 (which is incorporated herein by reference).

Usually, in situ mono- or diester dicarboxylate concentrate compositions of the invention will contain 0 to about 80 wt-% cosolvent, more preferably 0 to about 25 wt-% cosolvent, and most preferably 0 to about 20 wt-% cosolvent.

Surfactant

A variety of surfactants can be employed. In general, the surfactant identity and use level is selected based upon characteristics of the selected mono- or diester dicarboxylate and other additives, such as its solubility in the diluting solvent (usually water or a densified fluid such as carbon dioxide). Preferably, the surfactant does not tend to cause formation of insoluble deposits, and has low odor and low toxicity. Mixtures of surfactants can be used if desired.

Suitable surfactants include nonionic surfactants, anionic surfactants, cationic surfactants, amphoteric surfactants, amine oxides, and the like. Preferred surfactants include anionic surfactants and amine oxides. Preferred surfactants which can be employed include anionic surfactants such as alkyl sulfates and alkane sulfonates, linear alkyl benzene or naphthalene sulfonates, secondary alkane sulfonates, alkyl ether sulfates or sulfonates, alkyl phosphates or phosphonates, dialkyl sulfosuccinic acid esters, sugar esters (e.g., sorbitan esters), amine oxides (mono-, di-, or tri-alkyl) and $C_8$–$C_{10}$ alkyl glucosides.

Other surfactants for use in the present invention include n-octanesulfonate, available as NAS 8D from Ecolab, n-octyl dimethylamine oxide, n-decyl dimethyl amine oxide, cocoa dimethylamine oxide, and the commonly available aromatic sulfonates such as the alkyl benzene sulfonates (e.g. dodecylbenzene sulfonate, cumene sulfonate, xylene sulfonates) or naphthalene sulfonates.

The most preferred anionic surfactants include C6–C24 alkylbenzene sulfonates; C6–C24 olefin sulfonates; C6–C24 paraffin sulfonates; cumene sulfonate; xylene sulfonate; C6–C24 alkyl naphthalene sulfonates; C6–C24 alkyl or dialkyl diphenyl ether sulfonates or disulfonates, C4–C24 mono or dialkyl sulfosuccinates; sulfonated or sulfated fatty acids; C6–C24 alcohol sulfates (preferably C6–C12 alcohol sulfates); C6–C24 alcohol ether sulfates having 1 to about 20 ethylene oxide groups; and C4–C24 alkyl, aryl or alkaryl phosphate esters or their alkoxylated analogues having 1 to about 40 ethylene, propylene or butylene oxide units or mixtures thereof.

Other surfactants include nonionic surfactants of C6–C24 alcohol ethoxylates (preferably C6–C14 alcohol ethoxylates) having 1 to about 20 ethylene oxide groups (preferably about 9 to about 20 ethylene oxide groups); C6–C24 alkylphenol ethoxylates (preferably C8–C10 alkylphenol ethoxylates) having 1 to about 100 ethylene oxide groups (preferably about 12 to about 20 ethylene oxide groups); C6–C24 alkylpolyglycosides (preferably C6–C20 alkylpolyglycosides) having 1 to about 20 glycoside groups (preferably about 9 to about 20 glycoside groups); C6–C24 fatty acid ester ethoxylates, propoxylates or glycerides; and C4–C24 mono or dialkanolamides. A particularly useful nonionic surfactant for use as a defoamer is nonylphenol having an average of 12 moles of ethylene oxide condensed thereon, it being end capped with a hydrophobic portion comprising an average of 30 moles of propylene oxide.

More preferred surfactants include food grade surfactants, linear alkylbenzene sulfonic acids and their salts, and ethylene oxide/propylene oxide derivatives sold under the Pluronic™ trade name. Preferred cationic surfactants include quaternary ammonium compounds having the formula:

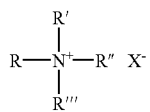

where R, R', R" and R'" are each a $C_1$–$C_{24}$ alkyl, aryl or aralkyl group that can optionally contain one or more P, O, S or N heteroatoms, and X is F, Cl, Br, I or an alkyl sulfate.

Preferred amphoteric surfactants include amine oxide compounds having the formula:

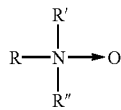

where R, R', R" and R'" are each a $C_1$–$C_{24}$ alkyl, aryl or aralkyl group that can optionally contain one or more P, O, S or N heteroatoms.

Another class of preferred amphoteric surfactants includes betaine compounds having the formula:

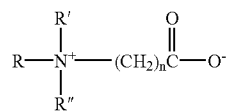

where R, R', R" and R'" are each a $C_1$–$C_{24}$ alkyl, aryl or aralkyl group that can optionally contain one or more P, O, S or N heteroatoms, and n is about 1 to about 10.

A most preferred surfactant would be compatible as an indirect or direct food additive or substance; especially those described in the Code of Federal Regulations (CFR), Title 21—Food and Drugs, parts 170 to 186 (which is incorporated herein by reference).

Usually, in situ mono- or diester dicarboxylate concentrate compositions of the invention will contain no more than about 25 wt-% surfactant, more preferably 0 to about 10 wt-% surfactant and most preferably 0 to about 5 wt-% surfactant. Use dilutions of these concentrates preferably contain no more than about 10 wt-% surfactant, more preferably 0 to about 5 wt-% surfactant, and most preferably 0 to about 2 wt-%. Most preferably, the concentrates are substantially surfactant-free.

Additional Antimicrobial Agent

The antimicrobial compositions of the invention can contain an additional antimicrobial agent. This additional antimicrobial agent can be dissolved or dispersed in the in situ mono- or diester dicarboxylate concentrate composition or in the diluting solvent. Suitable additional antimicrobial agents include sulfonic acids (e.g., dodecylbenzene sulfonic acid), iodo-compounds or active halogen compounds (e.g., iodine, interhalides, polyhalides, metal hypochlorites, hypochlorous acid, metal hypobromites, hypobromous acid, chloro- and bromo-hydantoins, chlorine dioxide and sodium chlorite), additional active oxygen compounds such as organic peroxides including benzoyl peroxide, alkyl benzoyl peroxides, ozone, singlet oxygen generators, phenolic derivatives (e.g., o-phenyl phenol, o-benzyl-p-chlorophenol, tert-amyl phenol and $C_1$–$C_6$ alkyl hydroxy benzoates), quaternary ammonium compounds (e.g., alkyldimethylbenzyl ammonium chloride, dialkyldimethyl ammonium chloride and mixtures thereof), and mixtures of such antimicrobial agents, in an amount sufficient to provide the desired degree of microbial protection. Most of the aforementioned additional antimicrobial agents having about 1–6 carbons, or an ionic charge, would be mostly soluble in the diluting solvent; those with higher carbon numbers would generally be more soluble in the in situ mono- or diester dicarboxylate concentrate composition.

Compositions of the invention containing such optional additional antimicrobial agents appear to have substantially greater antimicrobial effectiveness than comparison aqueous solutions or dispersions containing the additional antimicrobial agent alone. If present in the concentrated antimicrobial compositions of the invention, the additional antimicrobial agent preferably is 0.01 to about 30 wt-% of the composition, more preferably 0.05 to about 10 wt-% and most preferably about 0.1 to about 5 wt-%. In a use solution the additional antimicrobial agent preferably is 0.001 to about 5 wt-% of the composition, more preferably 0.01 to about 2 wt-%, and most preferably 0.05 to about 0.5 wt-%.

Adjuvants

The in situ composition of or employed in the method of the invention can also include any number of adjuvants. Specifically, the composition can include stabilizing agents, wetting agents, hydrotropes, thickeners, foaming agents, chelating agents, builders, pH adjusters, anticorrosion additives, antirust additives indicators as well as fragrances, pigments, or dyes among any number of constituents which can be added to the composition. Such adjuvants can be preformulated with the in situ composition or added to the system simultaneously, or even after, the addition of the in situ composition. The composition can also contain any number of other constituents as necessitated by the application, which are known to those of skill in the art and which can facilitate the activity of the present invention.

Stabilizing Agents

Stabilizing agents can be added to the composition, for example, to stabilize the peracid and hydrogen peroxide and prevent the premature oxidation of this constituent within the composition.

Chelating agents or sequestrants generally useful as stabilizing agents in the present compositions include salts or acids of (expressed in acid form) dipicolinic acid, picolinic acid, gluconic acid, quinolinic acid, and alkyl diamine polyacetic acid-type chelating agents such as ethylenediamine tetraacetic acid (EDTA), hydroxyethylethylethylene diamine triacetic acid (HEDTA), and ethylene triaminepentaacetic acid, acrylic and polyacrylic acid-type stabilizing agents, phosphonic acid, and phosphonate-type chelating agents among others. Preferable sequestrants include phosphonic acids and phosphonate salts including 1-hydroxy ethylidene-1,1-diphosphonic acid ($CH_3C(PO_3H_2)_2OH$) (HEDP), amino[tri(methylene phosphonic acid)] ($[CH_2PO_3H_2]_2$(ethylene diamine[tetra methylene-phosphonic acid)], 2-phosphene butane-1,2,4-tricarboxylic acid, as well as the alkyl metal salts, ammonium salts, or alkyloyl amine salts, such as mono, di, or tetra-ethanolamine salts.

The stabilizing agent can be used in a concentrate at a concentration typically ranging from about 0 wt-% to about 20 wt-% of the composition, preferably from about 0.1 wt-% to about 10 wt-% of the composition, and most preferably from about 0.2 wt-% to 5 wt-% of the composition. In a use solution they range from 0 wt-% to about 5 wt-% of the composition, preferably from 0 wt-% to about 2 wt-% of the composition, and most preferably from 0 wt-% to 0.5 wt-% of the composition Amino phosphates and phosphonates are also suitable for use as chelating agents in the compositions and include ethylene diamine (tetramethylene phosphonates), nitrilotrismethylene phosphates, diethylenetriamine (pentamethylene phosphonates). These amino phosphonates commonly contain alkyl or alkaline groups with less than 8 carbon atoms. The phosphonic acid may also include a low molecular weight phosphonopolycarboxylic acid such as one having about 2–4 carboxylic acid moieties and about 1–3 phosphonic acid groups. Such acids include 1-phosphono-1-methylsuccinic acid, phosphonosuccinic acid and 2-phosphonobutane-1,2,4-tricarboxylic acid.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino(tri(methylenephosphonic acid)), ($N[CH_2PO_3H_2]_3$), available from Monsanto as DEQUEST® 2000; ethylenediamine[tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The above-mentioned phosphonic acids can also be used in the form of water soluble acid salts, particularly the alkali metal salts, such as sodium or potassium; the ammonium salts or the alkylol amine salts where the alkylol has 2 to 3 carbon atoms, such as mono-, di-, or triethanolamine salts. If desired, mixtures of the individual phosphonic acids or their acid salts can also be used.

The concentration of chelating agent useful in a concentrate of the present invention generally ranges from 0 to about 10 wt-%, preferably from 0 to about 2 wt-%, more preferably from 0 to about 0.5 wt-%. In a use solution they can typically range from 0 wt-% to about 5 wt-% of the composition, preferably from 0 wt-% to about 1 wt-% of the composition, and most preferably from 0 wt-% to 0.5 wt-% of the composition.

Buffering Agents

Buffering agents can be added to the composition, for example, to stabilize the pH of an antimicrobial solution. While generally free of strong acids, the in situ compositions of the invention might include buffering adjuvants such as weak inorganic acids, organic acids, organic salts, and inorganic salts for buffering purposes. These might include an inorganic-based salt or weak inorganic acids including phosphates (including mono-, di-, or tri-basic potassium, calcium, or sodium phosphate), sulfates (including sodium, potassium, and magnesium sulfates), bisulfates, silicates (including sodium, potassium, and magnesium silicates), borates (including sodium or potassium borates, and boric acid), sulfamic acid; organic-based compounds such as malic acid, tartaric acid, citric acid, acetic acid, glycolic, glutamic acid, sorbic acid, benzoic acid, adipic acid, succinic acid, diacetate salts, or dimer and fatty acids; or mixtures thereof.

Additionally, carbonation acidification via the interaction of carbon dioxide with water is possible for aqueous formulations.

Some additional acids or salts that may be optionally added to the present invention for pH control, buffering, include aliphatic or olefinic carboxylic acids or carboxylate salts, aromatic carboxylic acids or carboxylic salts, inorganic acids or salts, polymeric carboxylic acids or carboxylate salts, organic-phosphonates, organic-phosphates or their salts, organic-sulfonates, organic-sulfates or their salts, organic boric acids or salts, amino acids or salts, or mixtures thereof. Most preferably the invention could include carboxylic acids, di/tri-carboxylic acids, hydroxy carboxylic acids, or alpha-hydroxy carboxylic acids—or their salts, anhydride, or esters—such as glycolic, lactic, malic, citric, tartaric, acetic, diacetate, butyric, octanoic, heptanoic, nonanoic, decanoic, malonic, adipic, succinic, salicylic, fumaric, maleic, acetoacetic, oxalacetic, pyruvic, α-ketoglutaric, and so forth. Preferably mild acids are used in the present invention.

Most preferred acid/salt combinations for use as buffers in the present invention include citric/citrate, phosphoric/phosphate, boric/borate, sulfuric/bisulfate, succinic/succinate buffer, or mixtures thereof, or any of these acids with any of the salts. The acid or buffer are, however, optional to the present in situ compositions.

Formulation of In situ Mono- or Diester Dicarboxylate Antimicrobial Compositions The compositions of or used in the methods of the invention can be formulated employing methods of the invention for making an in situ mono- or diester dicarboxylate antimicrobial composition of the invention. The method of the invention for making these antimicrobial compositions includes adding the desired ingredients to a vessel, mixing, and retaining them there for a period from, for example, a few minutes to a few days.

In a preferred embodiment, the present method for making an antimicrobial composition includes adding hydrogen peroxide and mono- or diester dicarboxylate to a vessel. Preferably, the method includes mixing the hydrogen peroxide and mono- or diester dicarboxylate. After adding, the hydrogen peroxide and the mono- or diester dicarboxylate can be retained in the vessel. They can be retained for a wide range of times, including from a few minutes to not more than few days. Preferably, retaining has a duration of from 0.05 minutes to no more than about 21 days, more preferably from about 0.5 minutes to about 72 hours. The retention time can be shorter if the composition includes catalyst and the temperature is raised. For example, the system can be heated between about 30° C. to about 100° C.

After retaining, the composition including the hydrogen peroxide and mono- or diester dicarboxylate can be prepared for use, such as by removing from the vessel and/or diluting to a suitable concentration of mono- or diester dicarboxylate and hydrogen peroxide for antimicrobial effect on an object. Preferably, the present method includes diluting the retained and mixed hydrogen peroxide and mono- or diester dicarboxylate composition to form a use antimicrobial composition. The in situ composition can be diluted as described below for use compositions.

By simultaneously and/or alternately adding and removing ingredients and composition from the vessel, the method of making the antimicrobial composition can be carried out continuously, semi continuously, or batch wise. For example, the method can include continuously adding hydrogen peroxide and continuously adding mono- or diester dicarboxylate to the vessel. By way of further example, the method can also include continuously removing a portion of the retained and mixed hydrogen peroxide and mono- or diester dicarboxylate composition from the vessel for diluting. Alternatively, the method can include periods of continuous adding or continuous removing interrupted by periods where adding and/or removing are halted. Such periodic continuous addition or removing can be referred to as semi continuous addition or removing. In another alternative, batches of ingredients can be added and batches of composition can be removed as required.

The ingredients are typically added to achieve an in situ mono- or diester dicarboxylate concentrate composition of the present invention. The present method can add any of a variety of ingredients to form an in situ mono- or diester dicarboxylate composition of the present invention. For example, the method can add any of a variety of mono- or diester dicarboxylates, as described herein.

Preferably, the method includes adding as hydrogen peroxide and aqueous solution including 0.01 wt-% to about 35 wt-%, or sometimes to about 50%, preferably about 1 wt-% to about 35 wt-%, and most preferably 2 wt-% to about 35 wt-%, hydrogen peroxide. Other hydrogen peroxide compositions are suitable for use in the present method, including hydrogen peroxide in other solvents or more or less concentrated aqueous solutions. Water is typically added only as the solvent for the hydrogen peroxide, or as a solvent for any adjuvants (e.g., stabilizing agents), cosolvents, or surfactants. However, additional water can be added if necessary or desired.

The ingredients of the composition can be added to, mixed in, retained in, and/or removed from any of a variety of vessels suitable for holding and mixing compositions including hydrogen peroxide, mono- or diester dicarboxylate, and, optionally, ester peroxycarboxylic acid. For example, the vessel can be a tank, a pipe, a reservoir, a flask, a tube, or the like. The ingredients of the composition can be mixed by any of a variety of an apparatus suitable for mixing a composition including hydrogen peroxide, mono- or diester dicarboxylate, and, optionally, ester peroxycarboxylic acid. For example, mixing can be accomplished employing a stirrer, paddles, recirculation or transfer pumps, fogging systems, in-line static mixers, magnetic mixers, jets, or the like.

Use Compositions

The invention contemplates an in situ mono- or diester dicarboxylate composition which is diluted to a use solution prior to application to an object. The level of active components in the concentrate composition can depend on the intended dilution factor and the desired level of antimicrobial activity. Generally, a dilution of 0.01 to about 50, preferably 0.1 to about 20, and most preferably 0.5 to about 10 fluid ounces to about 10 gallons of water is used for aqueous antimicrobial compositions. Higher use dilutions can be employed if elevated temperatures (greater than 25° C.) or extended exposure time (greater than 10 seconds) can be employed. In the typical use locus, the concentrate is diluted with a major proportion of water using commonly available tap or service water mixing the materials at a dilution ratio of about 0.1 to about 5 ounces of concentrate per 10 gallons of water.

An aqueous antimicrobial sanitizing use solution comprises at least about 50 part per million (ppm), preferably about 500 ppm, and most preferably about 1500 ppm of in situ mono- or diester dicarboxylate composition. Preferably, adding water or other diluting solvent or gas, will yield a composition including 0.01 wt-% to about 20 wt-%, preferably 0.1 wt-% to about 10 wt-%, and more preferably 0.5 wt-% to about 7 wt-% mono- or diester dicarboxylate; 0.01 wt-% to about 20 wt-%, preferably 0.5 wt-% to about 12 wt-%, and more preferably 0.5 wt-% to about 7 wt-%, hydrogen peroxide; optionally 0 to 5 wt-%, preferably 0 to about 2 wt-%, and more preferably 0 to about 1 wt-% stabilizer such as HEDP or similar catalyst; optionally 0 to 10 wt-%, preferably 0.5 wt-% to about 5 wt-%, and more preferably 0 to about 2 wt-% surfactants, 0 to 10 wt-%, preferably 0 to about 5 wt-%, and more preferably 0 to about 2 wt-% buffering agents. Higher levels can be employed in the use solution to obtain disinfecting or sterilizing results.

A variety of fluids can be used as the diluting solvent for forming the use composition. Suitable diluting solvents include water in its liquid form; steam; condensed gases and other supercritical fluids (e.g., $CO_2$); perchloroethylene; oils such as silicone oils (e.g., siloxanes), gear oils, transaxle oils, mineral oils or vegetable oils; and carboxylic esters such as methyl soyate. Mixtures of diluting solvents can be used if desired. Especially useful oils include food grade or food-derived oils, flavorings, or fragrance oils. Preferably, the diluting solvent consists essentially of or consists of water in its liquid form.

Methods Employing the In Situ Ester Peroxycarboxylic Acid Compositions

The antimicrobial compositions of the invention can be used for a variety of domestic or industrial applications, e.g., to reduce microbial or viral populations on a surface or object or in a body or stream of water. The compositions can be applied in a variety of areas including kitchens, bathrooms, factories, hospitals, dental offices, pharmaceutical plants or co-packers, and food plants or co-packers, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials comprising, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces can be made from a variety of materials comprising, for example, paper, fiber, woven or nonwoven fabric, soft plastics and elastomers. The compositions of the invention can also be applied to soft surfaces such as food and skin.

The antimicrobial compositions of the invention can be included in products such as sterilants, sanitizers, disinfectants, preservatives, deodorizers, antiseptics, fungicides, germicides, sporicides, virucides, detergents, bleaches, hard surface cleaners, hand soaps and pre- or post-surgical scrubs.

The antimicrobial compositions can also be used in veterinary products such as mammalian skin treatments or in products for sanitizing or disinfecting animal enclosures, pens, watering stations, and veterinary treatment areas such as inspection tables and operation rooms.

The present in situ compositions can be employed for reducing the population of pathogenic microorganisms, such as pathogens of humans, animals, and the like. The in situ compositions can exhibit activity against pathogens including fungi, molds, bacteria, spores, and viruses, for example, parvovirus, coxsackie virus, herpes virus, *S. aureus, E. coli, Streptococci, Legionella,* mycobacteria, or the like. Such pathogens can cause a varieties of diseases and disorders, including athletes foot, hairy hoof wart disease, Mastitis or other mammalian milking diseases, tuberculosis, and the like. The compositions of the present invention can reduce the population of microorganisms on skin or other external or mucosal surfaces of an animal. In addition, the present compositions can kill pathogenic microorganisms that spread through transfer by water, air, or a surface substrate. The composition need only be applied to the skin, other external or mucosal surfaces of an animal water, air, or surface.

The antimicrobial compositions can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like. Particular foodstuffs that can be treated with compositions of the invention include eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels. The present composition is useful in the cleaning or sanitizing of containers, processing facilities, or equipment in the food service, food processing, beverage, dairy, brewery, and pharmaceutical industries. The antimicrobial compositions have particular value for use on food, beverage, and pharmaceutical packaging materials and equipment, and especially for cold or hot aseptic packaging. Examples of process facilities in which the composition of the invention can be employed include a milk line dairy, a continuous brewing system, food processing lines such as pumpable food systems and beverage lines, pharmaceutical fill lines or tabletizers and bottlers, etc. Food service wares can be disinfected with the composition of the invention. For example, the compositions can also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET, various copolymers, bottles of various volumes (100 ml to 2 liter, etc.), one gallon milk containers, aluminum foil, paper board juice or milk containers, etc. A detailed description of additional treatable food, beverage, and pharmaceutical packaging container materials are found in the Code of Federal Regulations, Title 21, parts 175 to 178.

The antimicrobial compositions can also be used on or in other industrial equipment and in other industrial process streams such as heaters, cooling towers, boilers, retort waters, rinse waters, aseptic packaging wash waters for foods, pharmaceuticals, and beverages, and the like. The compositions can be used to treat microbes and odors in recreational waters such as in pools, spas, recreational flumes and water slides, fountains, and the like.

A filter containing the composition can reduce the population of microorganisms in air and liquids. Such a filter can remove water and air-born pathogens such as *Legionella*.

Other hard surface cleaning applications for the antimicrobial compositions of the invention include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like.

Generally, the actual cleaning of the in-place system or other surface (i.e., removal of unwanted offal therein) is accomplished with a different material such as a formulated detergent which is introduced with heated water. After this cleaning step, the instant sanitizing composition would be applied or introduced into the system at a use solution concentration in unheated, ambient temperature water. CIP typically employ flow rates on the order of about 40 to about 600 liters per minute, temperatures from ambient up to about 70° C., and contact times of at least about 10 seconds, more preferably about 30 to about 120 seconds. The present sanitizing composition is found to remain in solution in cold (e.g., 40° F./4° C.) water and heated (e.g., 140° F./60° C.) water. Although it is not normally necessary to heat the aqueous use solution of the present composition, under some circumstances heating may be desirable to further enhance its antimicrobial activity. These materials are useful at any conceivable temperatures.

A method of sanitizing substantially fixed in-place process facilities comprises the following steps. The use composition of the invention is introduced into the process facilities at a temperature in the range of about 4° C. to 60° C. After introduction of the use solution, the solution is held in a container or circulated throughout the system for a time sufficient to sanitize the process facilities (i.e., to kill undesirable microorganisms). After the surfaces have been sanitized by means of the present composition, the use solution is drained. Upon completion of the sanitizing step, the system optionally may be rinsed with other materials such as potable water. The composition is preferably circulated through the process facilities for 10 minutes or less.

The composition may also be employed by dipping food processing equipment into the use solution, soaking the equipment for a time sufficient to sanitize the equipment, and wiping or draining excess solution off the equipment, The composition may be further employed by spraying or wiping food processing surfaces with the use solution, keeping the surfaces wet for a time sufficient to sanitize the surfaces, and removing excess solution by wiping, draining vertically, vacuuming, etc.

The composition of the invention may also be used in a method of sanitizing hard surfaces such as institutional type equipment, utensils, dishes, health care equipment or tools, and other hard surfaces. The composition may also be employed in sanitizing clothing items or fabric which have become contaminated. The use composition is contacted with any of the above contaminated surfaces or items at use temperatures in the range of about 4° C. to 60° C., for a period of time effective to sanitize, disinfect, or sterilize the surface or item. For example, the concentrate composition can be injected into the wash or rinse water of a laundry machine and contacted with contaminated fabric for a time sufficient to sanitize the fabric. Excess solution can then be removed by rinsing or centrifuging the fabric.

The antimicrobial compositions can be applied to microbes or to soiled or cleaned surfaces using a variety of methods. These methods can operate on an object, surface, in a body or stream of water or a gas, or the like, by contacting the object, surface, body, or stream with an in situ mono- or diester dicarboxylate composition of the invention. Contacting can include any of numerous methods for applying a composition, such as spraying the composition, immersing the object in the composition, foam or gel treating the object with the composition, fogging, atomizing, or aerosolizing, or a combination thereof.

A concentrate or use concentration of an in situ mono- or diester dicarboxylate composition of the present invention can be applied to or brought into contact with an object by any conventional method or apparatus for applying an antimicrobial or cleaning composition to an object. For example, the object can be wiped with, sprayed with, and/or immersed in the in situ composition, or a use composition made from the in situ composition. The in situ composition can be sprayed or wiped onto a surface; the composition can be caused to flow over the surface, or the surface can be dipped into the composition. Contacting can be manual or by machine.

The compositions can be formulated as liquids, gels, aerosols, waxes, solids, or powders. If steam or another gaseous diluting solvent is employed, then the compositions can be formulated to be applied in a gaseous state.

Methods for Beverage, Food, and Pharmaceutical Processing

The peroxyacid sanitizing materials of the invention can be used in the manufacture of beverage, food, and pharmaceutical materials including fruit juice, dairy products, malt beverages, soybean-based products, yogurts, baby foods, bottled water products, teas, cough medicines, drugs, and soft drinks. The materials can be used to sanitize bottles, pumps, lines, tanks and mixing equipment used in the manufacture of such beverages. Further, the peroxyacid materials can be used in aseptic, cold filling operations in which the interior of the food, beverage, or pharmaceutical container is sanitized prior to filling. In such operations, a container is contacted with the sanitizing in situ mono- or diester dicarboxylate composition material, typically using a spray, or dipping, or filling device to intimately contact the inside of then container with the in situ mono- or diester dicarboxylate composition, for sufficient period of time to reduce microorganism populations within the container. The container is then emptied of the amount of sanitizer used. After emptying, the container can then be commonly rinsed with potable water or sterilized water and again emptied; however, this is not a required step of the current invention. After rinsing, the container is then filled with the beverage, food, or pharmaceutical. The container is then sealed, capped or closed and then packed for shipment for ultimate sale. The sealed container can be autoclaved or retorted for added microorganism kill.

In food, beverage, or pharmaceutical manufacturing, fungal microorganisms of the genus *Chaetomium* or *Arthrinium*, and spores or bacterial of the genus *Bacillus* spp. can be a significant problem in bottling processes, particularly in cold aseptic bottling processes. The in situ mono- or diester dicarboxylate sanitizer materials of the invention can be used for the purpose of controlling or substantially reducing (by more than a 5 $\log_{10}$ reduction) the number of *Chaetomium* or *Arthrinium* or *Bacillus* microorganisms in beverage or food or pharmaceutical bottling lines using cold aseptic bottling techniques.

In such techniques, metallic, aluminum or steel cans can be filled, glass bottles or containers can be filled, or plastic (PET or PBT or PEN) bottles, and the like can be filled using cold aseptic filling techniques. In such processes, the in situ mono- or diester dicarboxylate materials of the invention can be used to sanitize the interior of beverage containers prior to filling with the carbonated beverage. Typical carbonated beverages in this application include cola beverage, fruit beverages, ginger ale beverages, root beer beverages, iced tea beverages which may be non-carbonated, and other common beverages considered soft drinks. The in situ mono- or diester dicarboxylate materials of the invention can be used to sanitize both the tanks, lines, pumps, and other equipment used for the manufacture and storage of the soft drink material and also used in the bottling or containers for the beverages. The in situ mono- or diester dicarboxylate sanitizing materials are useful for killing both bacterial and fungal microorganisms that can be present on the surfaces of the production equipment and beverage containers.

The present invention is based upon the surprising discovery that in situ mono- or diester dicarboxylate compositions can effectively kill microorganisms (e.g., >1 $\log_{10}$ and especially a 5 $\log_{10}$ reduction in 30 seconds) from a concentration level of at least about 50 part per million (ppm), preferably about 500 ppm, and most preferably about 1500 ppm of in situ mono- or diester dicarboxylate composition. Typically the in situ mono- or diester dicarboxylate composition, excluding water, would be present at a concentration of 0.01 to about 50 wt-%, preferably 0.1 to about 10 wt-%, and most preferably 0.5 to about 5 wt-%.

The Figure shows a schematic for an embodiment of a bottle spraying/bottling operation using in situ mono- or diester dicarboxylate composition including a cold aseptic operation. In the figure, a plant 100 that can contact beverage bottles with an in situ mono- or diester dicarboxylate composition for a sanitizing regime is shown. In the figure, bottles 110 are passed through a sterilizing tunnel 102. The sanitized bottles 110*a* then pass through a rinsing tunnel 103 and emerge as sanitized rinsed bottles 110*b*.

In the process, bulk in situ mono- or diester dicarboxylate composition is added to a holding tank 101. Commonly, the materials are maintained at a temperature of about 22° C. in tank 101. To obtain the effective use concentration of the in situ mono- or diester dicarboxylate composition, make-up water 105 is combined with the concentrated in situ mono- or diester dicarboxylate composition into the tank 101. The in situ mono- or diester dicarboxylate use composition is passed through a heater 108 to reach a temperature of about 45–50° C. The heated in situ mono- or diester dicarboxylate use composition is sprayed within sterilizing tunnel 102 into and onto all surfaces of the bottle 110. An intimate contact between the in situ mono- or diester dicarboxylate composition and the bottle 110 is essential for reducing microbial populations to a sanitizing level.

After contact with the in situ mono- or diester dicarboxylate use composition and after dumping any excess composition from the bottles, the sanitized bottles 110 are then passed to a fresh water rinse tunnel 103. Fresh water 108 is provided from a fresh water make-up into a spray rinsing tunnel 103. Excess spray drains from rinsing tunnel 103 to drain 106. Within the tunnel 103, sanitized bottles 110a are thoroughly rinsed with fresh water. The complete removal of the in situ mono- or diester dicarboxylate composition from the bottles 110a is important for maintaining high quality of the beverage product. The rinsed and sanitized bottles 110b are then removed from the rinsing tunnel.

The day tank 101, the sterilizing tunnel 102 and the rinsing tunnel 103 are all respectively vended to wet scrubber or vent 111a, 111b or 111c to remove vapor or fumes from the system components. The sanitizer material that has been sprayed and drained from the bottles 110a accumulate in the bottom of the spray tunnel 102 and is then recycled through recycle line and heater 107 into the day tank 101.

The day tank is used for diluting, storing, and delivering the in situ mono- or diester dicarboxylate use composition which can include 0.01 to about 50 wt-%, preferably 0.1 to about 10 wt-%, and most preferably 0.5 to about 5 wt-% in situ mono- or diester dicarboxylate composition. All active treating equipment should be vented to a wet scrubber to prevent fumes from entering the atmosphere from the treatment equipment. Draining of the containers of their in situ mono- or diester dicarboxylate composition is important to reduce carry over minimized product loss. The contact between the bottles and the peroxyacid material is typically at a temperature of greater than about 0° C., more typically greater than 25° C., and most typically greater than about 40° C. Often temperatures between about 40° C. and 90° C. are used. To obtain sanitization of beverage containers at about 200 ppm to about 10,000 ppm, more preferably 500 ppm to about 5,000 ppm, and most preferably 700 ppm to about 2,500 ppm in situ mono- or diester dicarboxylate composition, contact at 40° C. to 60° C. for at least 5 sec, more preferably 10 sec, contact time is required.

Sanitizing conditions are greatly dependent on the processing temperatures, times, soil loading, water quality, and the like. Preferably, the sanitization equipment, day tank, sanitizing tunnel and rinsing tunnel are manufactured from polyolefin structural plastics, passivated stainless steel, or other non-corrosion sensitive production materials.

In the cold aseptic filling of 16 ounce polyethylene terephthalate (PET bottle), or other polymeric, beverage containers, a process has been adopted using an in situ mono- or diester dicarboxylate composition. The in situ mono- or diester dicarboxylate composition is diluted to a use concentration of about 0.1 to about 10 wt % and is maintained at an effective elevated temperature of about 25° C. to about 70° C., preferably about 40° C. to about 60° C. The spray or flood of the bottle with the material ensures contact between the bottle and the sanitizer material for at least 5, preferably 10, seconds. After flooding is complete, the bottle is drained of all contents for a minimum of 2 seconds and optionally followed by a 5 second water rinse with sterilized water using about 200 milliliters of water at 38° C. (100° F.). If optionally filled with the rinse water, the bottle is then drained of the sterilized water rinse for at least 2 seconds and is immediately filled with liquid beverage. After the rinse is complete, the bottles usually maintain less than 10, preferably 3, milliliters of rinse water after draining.

Methods for Contacting a Food Product

The present method and system provide for contacting a food product with an in situ composition employing any method or apparatus suitable for applying an in situ composition. For example, the method and system of the invention can contact the food product with a spray of an in situ composition, by immersion in the in situ composition, by foam or gel treating with the in situ composition, or the like. Contact with a spray, a foam, a gel, or by immersion can be accomplished by a variety of methods known to those of skill in the art for applying antimicrobial agents to food. These same methods can also be adapted to apply the in situ compositions of the invention to other objects.

The present methods require a certain minimal contact time of the composition with food product for occurrence of significant antimicrobial effect. The contact time can vary with concentration of the use composition, method of applying the use composition, temperature of the use composition, amount of soil on the food product, number of microorganisms on the food product, type of antimicrobial agent, or the like. Preferably the exposure time is at least about 5 to about 15 seconds.

A preferred method for washing food product employs a pressure spray including the in situ composition. During application of the spray solution on the food product, the surface of the food product can be moved with mechanical action, preferably agitated, rubbed, brushed, etc. Agitation can be by physical scrubbing of the food product, through the action of the spray solution under pressure, through sonication, or by other methods. Agitation increases the efficacy of the spray solution in killing micro-organisms, perhaps due to better exposure of the solution into the crevasses or small colonies containing the micro-organisms. The spray solution, before application, can also be heated to a temperature of about 15 to 20° C., preferably about 20 to 60° C. to increase efficacy. The spray in situ composition can be left on the food product for a sufficient amount of time to suitably reduce the population of microorganisms, and then rinsed, drained, or evaporated off the food product.

Application of the material by spray can be accomplished using a manual spray wand application, an automatic spray of food product moving along a production line using multiple spray heads to ensure complete contact, or other spray apparatus. One preferred automatic spray application involves the use of a spray booth. The spray booth substantially confines the sprayed composition to within the booth. The production line moves the food product through the entryway into the spray booth in which the food product is sprayed on all its exterior surfaces with sprays within the booth. After a complete coverage of the material and drainage of the material from the food product within the booth, the food product can then exit the booth. The spray booth can include steam jets that can be used to apply the in situ compositions of the invention. These steam jets can be used in combination with cooling water to ensure that the treatment reaching the food product surface is less than 65° C., preferably less than 60° C. The temperature of the spray on the food product is important to ensure that the food product is not substantially altered (cooked) by the temperature of the spray. The spray pattern can be virtually any useful spray pattern.

Immersing a food product in a liquid in situ composition can be accomplished by any of a variety of methods known to those of skill in the art. For example, the food product can be placed into a tank or bath containing the in situ composition. Alternatively, the food product can be transported or processed in a flume of the in situ composition. The washing solution is preferably agitated to increase the efficacy of the solution and the speed at which the solution reduces micro-organisms accompanying the food product. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the food product has been immersed for a time sufficient for the desired antimicrobial effect, the food product can be removed from the bath or flume and the in situ composition can be rinsed, drained, or evaporated off the food product.

In another alternative embodiment of the present invention, the food product can be treated with a foaming version of the composition. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines and alkyl amides. The foaming surfactant is typically mixed at time of use with the washing solution. Use solution levels of the foaming agents is from about 50 ppm to about 2 wt-%. At time of use, compressed air can be injected into the mixture, then applied to the food product surface through a foam application device such as a tank foamer or an aspirated wall mounted foamer.

In another alternative embodiment of the present invention, the food product can be treated with a thickened or gelled version of the composition. In the thickened or gelled state the washing solution remains in contact with the food product surface for longer periods of time, thus increasing the antimicrobial efficacy. The thickened or gelled solution will also adhere to vertical surfaces. The composition or the washing solution can be thickened or gelled using existing technologies such as: xanthan gum, polymeric thickeners, cellulose thickeners, or the like. Rod micelle forming systems such as amine oxides and anionic counter ions could also be used. The thickeners or gel forming agents can be used either in the concentrated product or mixing with the washing solution, at time of use. Typical use levels of thickeners or gel agents range from about 100 ppm to about 10 wt-%.

The present invention may be better understood with reference to the following examples. These examples are intended to be representative of specific embodiments of the invention, and are not intended as limiting the scope of the invention.

EXAMPLES

Example 1

Compositions According to the Present Invention Exhibit New and Potent Effects Against Microorganisms Applicants have demonstrated that compositions according to the present invention achieve properties distinct from the properties of conventional compositions containing mono- or diester dicarboxylates and ester peroxycarboxylic acids.

The present example employed several formulations of the previously available mixture of diester dicarboxylates and ester peroxycarboxylic acids (plus sulfuric acid, hydrogen peroxide, and water) sold under the trade name Perestane™ (by SOLVAY S. A., a company organized and existing under the laws of Belgium whose registered office is at 33 rue du Prince Albert, B-1050 Brussels, Belgium) and described in PCT patent publication WO 9828267(A1). As shown in Table 1 below, these conventional formulations have negligible activity against the microbes *Bacillus subtilis* and *Chaetomium funicola* (e.g., run no. 1). Surfactant blends of the commercial Perestane are similarly ineffective (e.g., run nos. 2–10, 13). Similarly, solvent blends of the commercial Perestane are unsuccessful (e.g., run nos. 11–13).

In contrast, compositions of and made according to the present invention exhibit excellent reduction of both *Chaetomium funicola* and *Bacillus subtilis*. The levels of reduction recorded in the table were achieved after 10 seconds of contact with the microorganism at 60° C.

TABLE 1

Compositions of the invention have antimicrobial activity not observed for conventional compositions.

| Run No. | Antimicrobial Bottle Wash System | Peracid Concentration (ppm) | Log Reduction C. funicola | Log Reduction B. subtilis |
|---|---|---|---|---|
| | Conventional Formulations | | | |
| 1 | Perestane[1] | 7000 ppm | 0.2 | — |
| 2 | Perestane[1] + | 1000 ppm | <0.2 | <0.2 |
| 3 | 3% Pluronic L61[2] | 2000 ppm | <0.2 | <0.2 |
| 4 | | 4000 ppm | <0.2 | <0.2 |
| 5 | Perestane[1] + | 1000 ppm | <0.2 | <0.2 |
| 6 | 3% Pluronic L61[2] + | 2000 ppm | <0.2 | <0.2 |
| 7 | 1% dodecylbenzene sulfonate | 4000 ppm | <0.2 | <0.2 |
| 8 | Perestane[1] + | 1000 ppm | <0.2 | <0.2 |
| 9 | 2.5% alcohol ethoxylate[3] + | 2000 ppm | <0.2 | <0.2 |
| 10 | 2.5% dodecylbenzene sulfonate[2] | 4000 ppm | <0.2 | <0.2 |
| 11 | Perestane[1] + 1% benzyl alcohol | 4000 ppm | 0.2 | — |
| 12 | Perestane[1] + 1% DBE[4] | 4000 ppm | 0.4 | — |
| 13 | Perestane[1] + 1% benzyl alcohol + surfactants[5] | 4000 ppm | 0.3 | — |

TABLE 1-continued

Compositions of the invention have antimicrobial activity not observed for conventional compositions.

| Run No. | Antimicrobial Bottle Wash System | Peracid Concentration (ppm) | Log Reduction | |
|---|---|---|---|---|
| | | | C. funicola | B. subtilis |
| In situ Compositions According to the Present Invention[6] | | | | |
| 11 | DBE-3[4] + $H_2O_2$ formula 1[7] | variable[6] | >4.4 | 2.9 |
| 12 | DBE-3[4] + $H_2O_2$ formula 2[8] | 1000–4000 ppm | >4.4 | >6.0 |

[1]Perestane is a tradename for a conventional, commercial blend of mono- or diester dicarboxylates and ester peroxycarboxylic acids that is sold by Solvay, see above.
[2]Pluronic L61 (BASF).
[3]Tergitol 15-S-9 (Union Carbide)
[4]Diester dicarboxylate blend (Dupont Nylon).
[5]Mixture containing 50% benzyl alcohol, 15% DOWANOL PPH ™ glycol solvent (Dow Chemical Co.), 15% BUTYL CARBITOL ™, 15% DOWANOL DPNB ™ glycol solvent (Dow Chemical Co.) and 5% SURFONIC 24-9 ™ nonionic surfactant (Huntsman Chemicals).
[6]The solution was aged >18 hours prior to use.
[7]Diester dicarboxylate blend (Dupont Nylon). The composition included 5.0% wt-% diester dicarboxylate, 2.1 wt-% $H_2O_2$, water.
[8]Diester dicarboxylate blend (Dupont Nylon). The composition included 5.0% wt-% diester dicarboxylate, 4.2 wt-% $H_2O_2$, water.

Data reported in Table 2 (below) indicate that the in situ compositions of, and made according to, the present invention can be mixed in a range of formulations to yield effective (>1.0 $\log_{10}$) microbial reductions at various reactant concentrations, reaction times, and temperatures. This substantial effect contrasts with the conventional Perestane™ compositions, which yielded less than 0.2 $\log_{10}$ reduction in the test organisms. Some of the present compositions have greater effect against *Bacillus cereus*, others against *Chaetomium funicola*. These data demonstrate that the present compositions have a broad spectrum of activity and perform in a broad-scope manner, and the conventional compositions do not.

TABLE 2

Compositions of the invention have antimicrobial activity against both C. funicola and B. cereus.

| Diester Dicarboxylate[1] wt-% | $H_2O_2$ wt-% | T °C. | Seconds of Contact | $\log_{10}$ Reduction |
|---|---|---|---|---|
| *C. funicola* | | | | |
| 2.0 | 0.56 | 40 | 120 | 0.3 |
| 2.5 | 0.70 | 40 | 120 | 0.8 |
| 3.0 | 0.84 | 40 | 120 | 1.0 |
| 2.0 | 0.56 | 60 | 10 | 0.7 |
| 2.5 | 0.70 | 60 | 10 | 1.8 |
| 3.0 | 0.84 | 60 | 10 | 2.8 |
| 5.0 | 2.1 | 60 | 10 | >4.4 |
| 5.0 | 4.2 | 60 | 10 | >4.4 |
| 4.0 | 2.0 | 60 | 10 | >4.4 |
| 4.0 | 4.0 | 60 | 10 | >4.4 |
| 5.0 | 2.0 | 60 | 10 | >4.4 |
| 5.0 | 4.0 | 60 | 10 | >4.4 |
| *B. cereus* | | | | |
| 2.0 | 0.56 | 40 | 120 | 2.9 |
| 2.5 | 0.70 | 40 | 120 | >6.3 |
| 3.0 | 0.84 | 40 | 120 | >6.3 |
| 2.0 | 0.56 | 60 | 10 | 1.3 |
| 2.5 | 0.70 | 60 | 10 | 2.6 |
| 3.0 | 0.84 | 60 | 10 | 4.2 |

[1]DBE-3 Diester dicarboxylate blend (Dupont Nylon).

Compositions of and made according to the present invention also exhibit excellent reduction of other microbes. For example, a composition including 5% mono-or-diester dicarboxylate (DBE3) and 3.0% hydrogen peroxide 2.4 log reduction against *N. fisheri* using a 10 second contact time and 60° C. For example, a composition including 5% mono- or diester dicarboxylate (DBE3) and 2.1% hydrogen peroxide and diluted to 100 ppm exhibited >7.1 log reduction against *Staphylococcus aureus*. The same composition at 60 ppm exhibited a log reduction of about 3.4 against this microorganism. Similarly, this composition at either 60 or 100 ppm exhibited >7.1 log reduction against *Escherichia coli*. At 30 ppm this composition exhibited a log reduction of about 2.7 against *E. coli*. These levels of reduction were achieved after 30 seconds contact with the microorganism at 25° C.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A composition comprising:
   about 1 wt-% to about 5 wt-% mono- or diester dicarboxylate,
   about 1 wt-% to about 4 wt-% hydrogen peroxide, and
   about 95 wt-% to about 98 wt-% water; and
   free of added strong acid,
   wherein the composition exhibits antimicrobial activity of greater than 2 $\log_{10}$ reduction against *Bacillus cereus, Baccillus subtilis,* or *Chaetomium funicola* upon contacting the microbe with the composition for at least 5 seconds at a temperature between about 0° C. and about 100° C.

2. The composition of claim 1, comprising:
   about 2 wt-% mono- or diester dicarboxylate,
   about 2 wt-% hydrogen peroxide, and
   about 95 wt-% water.

3. The composition of claim 1, wherein the mono-or-diester dicarboxylate comprises monomethyl malonate, dimethyl malonate, monoethyl malonate, diethyl malouiate, monopropyl unalonate, dipropyl malonate, monobutyl malonate, dibutyl malonate, diamyl malonate, dihexyl malonate, di-2-ethylliexyl malonate, monomethyl succinate, dimethyl succinate, monoethyl succinate, diethyl succinate, monopropyl succinate, dipropyl succinate, monobutyl succinate, dibutyl succinate, diamyl succinate, dihexyl succinate, di-2-ethylhexyl succinate, monomethyl glutarate, dimethyl glutarate, monoethyl glutarate, diethyl glutarate, monopropyl glutarate, dipropyl glutarate, monobutyl glutarate, dibutyl glutarate, diamyl glutarate, dihexyl glutarate, di-2-ethylhexyl glutarate, monomethyl adipate, dimethyl adipate, monoethyl adipate, diethyl adipate, monopropyl adipate, dipropyl adipate, monobutyl adipate, dibutyl adipate, diamyl adipate, dihexyl adipate, di-2-ethylhexyl adipate, monoethyl sebacate, dimethyl sebacate, monoethyl sebacate, diethyl sebacate, monopropyl sebacate, dipropyl sebacate, monobutyl sebacate, dibutyl sebacate, diamyl sebacate, dihexyl sebacate, di-2-ethylhexyl sebacate, or a mixture thereof.

4. The composition of claim 3, wherein the mono-or-diester dicarboxylate comprises dimethyl malonate, diethyl malonate, dipropyl malonate, dibutyl malonate, diamyl malonate, dihexyl malonate, di-2-ethylhexyl malonate, dimethyl succinate, diethyl succinate, dipropyl succinate, dibutyl succinate, diamyl succinate, dihexyl succinate, di-2-ethylhexyl succinate, dimethyl glutarate, diethyl glutarate, dipropyl glutarate, dibutyl glutarate, diamyl glutarate, dihexyl glutarate, di-2-ethylhexyl glutarate, dimethyl adipate, diethyl adipate, dipropyl adipate, dibutyl adipate, diamyl adipate, dihexyl adipate, di-2-ethylhexyl adipate, dimethyl sebacate, diethyl sebacate, dipropyl sebacate, dibutyl sebacate, diamyl sebacate, dihexyl sebacate, di-2-ethylhexyl sebacate, or a mixture thereof.

5. The composition of claim 4, wherein the mono-or-diester dicarboxylate comprises dimethyl oxalate, dimethyl malonate, dimethyl succinate, dimethyl adipate, dimethyl sebacate, diethyl oxalate, diethyl malonate, diethyl succinate, diethyl glutarate, diethyl adipate, diethyl sebacate, dipropyl oxalate, dipropyl malonate, dipropyl succinate, dipropyl glutarate, dipropyl adipate, dipropyl sebacate, dibutyl oxalate, dibutyl malonate, dibutyl succinate, dibutyl glutarate, dibutyl adipate, dibutyl sebacate, diamyl succinate, diamyl sebacate, dihexyl succinate, dihexyl sebacate, diethyihexyl succinate, diethyihexyl sebacate, or a mixture thereof.

6. The composition of claim 1, wherein the water is present at a level of about 95 wt-% to about 97 wt-%.

7. The composition of claim 1, further comprising a stabilizing agent.

8. The composition of claim 7, wherein the stabilizing agent comprises a phosphonic acid, a dipicolinic acid, a picolinic acid, a gluconic acid, a quinolinic acid, an ethylenediamine tetraacetic acid (EDTA), an hydroxyethylethyl-ethylene diamine triacetic acid (HEDTA), an ethylene triaminepentaacetic acid, a polyacrylic acid, a salt thereof, or a mixture thereof.

9. The composition of claim 8, wherein the phosphonate comprises 1-hydroxy ethylidene-1,1-diphosphonic acid ($CH_3C(PO_3H_2)_2OH$)(HEDP), amino[tri(methylene phosphonic acid)]([$CH_2PO_3H_2$]$_2$(ethylene diamine[tetra (methylene-phosphonic acid)], 2-phosphene butane-1,2,4-tricarboxylic acid, an alkali metal salt thereof, an ammonium salt thereof, an alkyloyl amine salt thereof, or a mixture thereof.

10. The composition of claim 9, wherein the alkyloyl amine salt comprises a monoethanol amine salt, a diethanolamine salt, a triethanolamine salt, or a mixture thereof.

11. A method for making an antimicrobial composition comprising:
adding hydrogen peroxide to a vessel;
adding mono- or diester dicarboxylate to a vessel;
mixing the hydrogen peroxide and the mono- or diester dicarboxylate in the vessel;
avoiding any addition of strong acid;
retaining the hydrogen peroxide and the mono- or diester dicarboxylate in the vessel for a duration of from about 0.05 minute to no more than about 21 days; and
diluting the retained and mixed hydrogen peroxide and mono- or diester dicarboxylate composition to form an antimicrobial composition comprising:
about 1 wt-% to about 5 wt-% mono- or diester dicarboxylate,
about 1 wt-% to about 4 wt-% hydrogen peroxide, and
about 95 wt-% to about 98 wt-% water; and
free of added strong acid,
wherein the composition exhibits antimicrobial activity of greater than 2 $\log_{10}$ reduction against *Bacillus cereus, Baccillus subtilis,* or *Chaetomium funicola* upon contacting the microbe with the composition for at least 5 seconds at a temperature between about 0° C. and about 100° C.

12. The method of claim 11, further comprising removing a portion of the retained and mixed hydrogen peroxide and mono- or diester dicarboxylate composition from the vessel far diluting.

13. The method of claim 11, comprising continuously, or semi-continuously, adding hydrogen peroxide and alternately continuously, or semi-continuously, adding mono-or-diester dicarboxylate to the vessel.

14. The method of claim 13 where hydrogen peroxide is added continuously, or semi-continuously, without adding additional mono-or-diester dicarboxylate to the vessel.

15. The method of claim 13, further comprising removing a portion of the retained and mixed hydrogen peroxide and mono-or-chester dicarboxylate composition from the vessel for diluting.

16. The method of claim 11, comprising batch wise adding hydrogen peroxide and batch wise adding mono- or diester dicarboxylate to the vessel.

17. The method of claim 11, comprising batch wise removing a portion of the retained and mixed hydrogen peroxide and mono- or diester dicarboxylate composition from the vessel for diluting.

18. A method of reducing population of microorganism on an object, comprising:
contacting the object with use composition of in situ composition;
the in situ composition comprising:
about 1 wt-% to about 5 wt-% mono- or diester dicarboxylate,
about 1 wt-% to about 4 wt-% hydrogen peroxide, and
about 95 wt-% to about 98 wt-% water; and
free of added strong acid,
wherein the composition exhibits antimicrobial activity of greater than 2 $\log_{10}$ reduction against *Bacillus cereus, Baccillus subtilis,* or *Chaetomium funicola* upon contacting the microbe with the composition for at least 5 seconds at a temperature between about 0° C. and about 100° C.

19. The method of claim 18, wherein the microorganism is a fungus.

20. The method of claim 18, wherein the microorganism is of the genus *Chaetomium.*

21. The method of claim 18, wherein the microorganism is of the genus *Arthrinium.*

22. The method of claim 18, wherein the microorganism is of the genus *Bacillus.*

23. The method of claim 18, comprising contacting with said use composition effective to reduce by more than 2-log order the population of spores and/or cells of *Bacillus cereus* within 10 seconds at 60° C.

24. The method of claim 18, comprising contacting with said use composition effective to reduce by more than 2-log order the population of spores and/or cells of *Chaetomium funicola* within 10 seconds at 60° C.

25. The method of claim 18, comprising contacting with said use composition effective to reduce by more than 2-log order the population of spores and/or cells of *Chaetomium funicola* and *Bacillus cereus* within 10 seconds at 60 ° C.

26. The method of claim 18, comprising contacting hard surface, soft surface, porous surface, food substance, or skin.

27. The method of claim 18, comprising contacting food, beverage, or pharmaceutical packaging.

28. The method of claim 27, comprising contacting aseptic food, beverage, or pharmaceutical packaging.

29. The method of claim 18, comprising contacting all or part of a food, beverage, or pharmaceutical plant.

30. The method of claim 18, comprising contacting tank, pipe, line, pump, valve, or other mixing or fluid transport apparatus.

31. A method for cold aseptic bottling of food, beverages, or pharmaceuticals, the method comprising:
   contacting an in situ composition for sufficient period of time to reduce the microorganism population;
      the in situ composition comprising:
         about 1 wt-% to about 5 wt-% mono- or diester dicarboxylate,
         about 1 wt-% to about 4 wt-% hydrogen peroxide, and
         about 95 wt-% to about 98 wt-% water; and
         free of added strong acid,
         wherein the composition exhibits antimicrobial activity of greater than 2 $\log_{10}$ reduction against *Bacillus cereus, Baccillus subtilis,* or *Chaetomium funicola* upon contacting the microbe with the composition for at least 5 seconds at a temperature between about 0° C. and about 100° C.;
   filling the container with a beverage, food, or pharmaceutical;
   sealing the filled container;
   wherein contacting obtains a significantly reduced population of microorganisms resulting in a sanitized food, beverage, or pharmaceutical container.

* * * * *